US010682354B2

(12) United States Patent
Wennogle

(10) Patent No.: US 10,682,354 B2
(45) Date of Patent: Jun. 16, 2020

(54) COMPOSITIONS AND METHODS

(71) Applicant: INTRA-CELLULAR THERAPIES, INC., New York, NY (US)

(72) Inventor: Lawrence P. Wennogle, Hillsborough, NJ (US)

(73) Assignee: INTRA-CELLULAR THERAPIES, INC., New York, NY (US)

(*) Notice: Subject to any disclaimer, the term of this patent is extended or adjusted under 35 U.S.C. 154(b) by 16 days.

(21) Appl. No.: 16/090,142

(22) PCT Filed: Mar. 28, 2017

(86) PCT No.: PCT/US2017/024575
§ 371 (c)(1),
(2) Date: Sep. 28, 2018

(87) PCT Pub. No.: WO2017/172795
PCT Pub. Date: Oct. 5, 2017

(65) Prior Publication Data
US 2019/0117658 A1 Apr. 25, 2019
US 2020/0022981 A9 Jan. 23, 2020

Related U.S. Application Data

(60) Provisional application No. 62/314,314, filed on Mar. 28, 2016.

(51) Int. Cl.
*A61K 31/498* (2006.01)
*A61K 31/517* (2006.01)
*A61K 31/519* (2006.01)
*A61K 31/4985* (2006.01)

(52) U.S. Cl.
CPC ........ *A61K 31/519* (2013.01); *A61K 31/4985* (2013.01)

(58) Field of Classification Search
CPC .......................... A61K 31/498; A61K 31/517
USPC ................................................ 514/250, 267
See application file for complete search history.

(56) References Cited

U.S. PATENT DOCUMENTS

| | | |
|---|---|---|
| 2,490,813 A | 12/1949 | Hughes et al. |
| 3,299,078 A | 1/1967 | Pachter et al. |
| 3,813,392 A | 5/1974 | Sellsdet et al. |
| 3,914,421 A | 10/1975 | Rajagopala |
| 4,001,263 A | 1/1977 | Plattner et al. |
| 4,115,577 A | 9/1978 | Rajagopala |
| 4,183,936 A | 1/1980 | Rajagopala |
| 4,219,550 A | 8/1980 | Rajagopala |
| 4,238,607 A | 12/1980 | Rajagopala |
| 4,389,330 A | 6/1983 | Tice et al. |
| 4,522,944 A | 6/1985 | Doria et al. |
| 4,530,840 A | 7/1985 | Tice et al. |
| 4,666,908 A | 5/1987 | Hamilton |
| 4,722,810 A | 2/1988 | Delaney et al. |
| 4,929,641 A | 5/1990 | Haslanger et al. |
| 4,971,971 A | 11/1990 | Tokunaga et al. |
| 4,985,432 A | 1/1991 | Tokunaga et al. |
| 5,114,976 A | 5/1992 | Norden |
| 5,151,419 A | 9/1992 | Perenyi et al. |
| 5,202,328 A | 4/1993 | De Laszlo et al. |
| 5,217,996 A | 6/1993 | Ksander |
| 5,294,612 A | 3/1994 | Bacon et al. |
| 5,393,755 A | 2/1995 | Neustadt et al. |
| 5,538,739 A | 7/1996 | Bodmer et al. |
| 5,576,460 A | 11/1996 | Buchwald et al. |
| 5,648,539 A | 7/1997 | Goodbrand et al. |
| 5,648,542 A | 7/1997 | Goodbrand et al. |
| 5,654,482 A | 8/1997 | Goodbrand et al. |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,824,683 A | 10/1998 | McKittrick et al. |
| 5,847,166 A | 12/1998 | Buchwald et al. |
| 5,849,770 A | 12/1998 | Head et al. |
| 5,902,901 A | 5/1999 | Goodbrand et al. |
| 5,939,419 A | 8/1999 | Tulshian et al. |
| 5,962,492 A | 10/1999 | Warrellow et al. |
| 6,013,621 A | 1/2000 | Nishi et al. |
| 6,043,370 A | 3/2000 | Kubo et al. |
| 6,133,273 A | 10/2000 | Gilbert et al. |
| 6,166,226 A | 12/2000 | Buchwald et al. |
| 6,221,335 B1 | 4/2001 | Foster |
| 6,235,742 B1 | 5/2001 | Bell et al. |
| 6,235,746 B1 | 5/2001 | Davis et al. |
| 6,235,936 B1 | 5/2001 | Buchwald et al. |

(Continued)

FOREIGN PATENT DOCUMENTS

| | | |
|---|---|---|
| DE | 19931206 | 1/2001 |
| DE | 10 2005 042877 | 3/2007 |

(Continued)

OTHER PUBLICATIONS

Adamo, et al., "Molecular targets for PDE inhibitor-mediated improvement of cardiac dysfunction in the mdx mouse?" BMC Pharmacology, 11(Suppl 1): O20 (2011) (Abstract only).
Ahn, H., et al., "Potent Tetracyclic Guanine Inhibitors of PDE1 and PDE5 Cyclic Guanosine Monophosphate Phosphodiesterases with Oral Antihypertensive Activity," J. Med. Chem., 40: 2196-2210 (1997).
Al-Afaleq, et al., "Heterocyclic o-Aminonitriles: Preparation of Pyrazolo[3,4-d]-pyrimidines with Modification of the Substituents at the 1-Position," Molecules, 6: 621-638 (2001).
Alvir, J., et al., "Clozapine-Induced Agranulocytosis," The New England Journal of Medicine, 329(3): 162-167 (1993).

(Continued)

*Primary Examiner* — Raymond J Henley, III
(74) *Attorney, Agent, or Firm* — Hoxie & Associates LLC

(57) ABSTRACT

The invention provides methods for the prophylaxis or treatment of one or more disorders associated with dementia comprising administering to a patient in need thereof, a therapeutically effective amount of (i) a 5-HT2A or 5-HT2A/D2 receptor ligand and (ii) a PDE1 inhibitor, and pharmaceutical compositions comprising (i) a 5-HT2A or 5-HT2A/D2 receptor ligand and (ii) a PDE1 inhibitor.

26 Claims, No Drawings

(56) References Cited

U.S. PATENT DOCUMENTS

| | | |
|---|---|---|
| 6,307,087 B1 | 10/2001 | Buchwald et al. |
| 6,316,444 B1 | 11/2001 | Hunt et al. |
| 6,323,366 B1 | 11/2001 | Wolfe et al. |
| 6,334,997 B1 | 1/2002 | Foster et al. |
| 6,395,916 B1 | 5/2002 | Buchwald et al. |
| 6,407,092 B1 | 6/2002 | Hester et al. |
| 6,492,371 B2 | 6/2002 | Roylance et al. |
| 6,423,716 B1 | 7/2002 | Matsuno et al. |
| 6,440,710 B1 | 8/2002 | Keinan et al. |
| 6,465,693 B2 | 10/2002 | Buchwald et al. |
| 6,498,165 B1 | 12/2002 | Armstrong et al. |
| 6,541,639 B2 | 4/2003 | Zhou et al. |
| 6,544,559 B2 | 4/2003 | Mesens et al. |
| 6,548,493 B1 | 4/2003 | Robichaud et al. |
| 6,552,017 B1 | 4/2003 | Robichaud et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,603,008 B1 | 8/2003 | Ando et al. |
| 6,649,608 B2 | 8/2003 | Pease et al. |
| 6,670,368 B1 | 12/2003 | Breault et al. |
| 6,693,099 B2 | 2/2004 | Degenhardt et al. |
| 6,699,852 B2 | 3/2004 | Robichaud et al. |
| 6,713,471 B1 | 3/2004 | Robichaud et al. |
| 6,756,373 B1 | 6/2004 | Allerton et al. |
| 6,759,554 B2 | 7/2004 | Buchwald et al. |
| 6,762,329 B2 | 7/2004 | Marcoux et al. |
| 6,849,619 B2 | 2/2005 | Robichaud et al. |
| 6,849,640 B2 | 2/2005 | Ennis et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 6,969,719 B2 | 11/2005 | Asberom et al. |
| 7,026,498 B2 | 4/2006 | Buchwald et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,153,824 B2 | 12/2006 | Palmer et al. |
| 7,157,451 B2 | 1/2007 | Atwal et al. |
| 7,183,282 B2 | 2/2007 | Robichaud et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,462,641 B2 | 12/2008 | Igo et al. |
| 7,517,990 B2 | 4/2009 | Ito et al. |
| 7,528,148 B2 | 5/2009 | Allen et al. |
| 7,579,324 B2 | 8/2009 | Burnet et al. |
| 7,592,454 B2 | 9/2009 | Lee et al. |
| 7,614,727 B2 | 11/2009 | Hori |
| 7,645,752 B2 | 1/2010 | McDevitt et al. |
| 7,964,607 B2 | 6/2011 | Verhoest et al. |
| 7,985,756 B2 | 7/2011 | Barlow et al. |
| 7,998,971 B2 | 8/2011 | Barlow et al. |
| 8,273,750 B2 | 9/2012 | Li et al. |
| 8,273,751 B2 | 9/2012 | Li et al. |
| 8,309,722 B2 | 11/2012 | Tomesch et al. |
| 8,461,148 B2 | 6/2013 | Hollander |
| 8,513,244 B2 | 8/2013 | Gendron et al. |
| 8,536,159 B2 | 9/2013 | Li et al. |
| 8,598,119 B2 | 12/2013 | Mates et al. |
| 8,633,180 B2 | 1/2014 | Li et al. |
| 8,648,077 B2 | 2/2014 | Tomesch et al. |
| 8,664,207 B2 | 3/2014 | Li et al. |
| 8,697,710 B2 | 4/2014 | Li et al. |
| 8,779,139 B2 | 7/2014 | Tomesch et al. |
| 8,791,138 B2 | 7/2014 | Seeman et al. |
| 8,829,008 B2 | 9/2014 | Li et al. |
| 8,846,693 B2 | 9/2014 | Li et al. |
| 8,858,911 B2 | 10/2014 | Li et al. |
| 8,859,564 B2 | 10/2014 | Li et al. |
| 8,871,792 B2 | 10/2014 | Hughes et al. |
| 8,927,556 B2 | 1/2015 | Li et al. |
| 8,993,572 B2 | 3/2015 | Mates et al. |
| 9,000,001 B2 | 4/2015 | Li et al. |
| 9,006,258 B2 | 4/2015 | Fienberg et al. |
| 9,073,936 B2 | 7/2015 | Li et al. |
| 9,157,906 B2 | 10/2015 | Greengard et al. |
| 9,168,258 B2 | 10/2015 | Mates et al. |
| 9,198,924 B2 | 12/2015 | Mates et al. |
| 9,199,995 B2 | 12/2015 | Tomesch et al. |
| 9,255,099 B2 | 2/2016 | Li et al. |
| 9,315,504 B2 | 4/2016 | Tomesch et al. |
| 9,371,324 B2 | 6/2016 | Mates et al. |
| 9,371,327 B2 | 6/2016 | Li et al. |
| 9,393,192 B2 | 7/2016 | Yam et al. |
| 9,403,836 B2 | 8/2016 | Li |
| 9,428,506 B2 | 8/2016 | Mates et al. |
| 9,434,730 B2 | 9/2016 | Li et al. |
| 9,468,637 B2 | 10/2016 | Fienberg et al. |
| 9,469,647 B2 | 10/2016 | Li et al. |
| 9,487,527 B2 | 11/2016 | Li et al. |
| 9,556,185 B2 | 1/2017 | Li et al. |
| 9,556,186 B2 | 1/2017 | Li et al. |
| 9,567,327 B2 | 2/2017 | Xiong et al. |
| 9,586,960 B2 | 3/2017 | Tomesch et al. |
| 9,598,426 B2 | 3/2017 | Li et al. |
| 9,605,041 B2 | 3/2017 | Greengard et al. |
| 9,616,061 B2 | 4/2017 | Mates et al. |
| 9,624,230 B2 | 4/2017 | Li et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,763,948 B2 | 9/2017 | Li et al. |
| 9,801,882 B2 | 10/2017 | Wennogle et al. |
| 9,884,872 B2 | 2/2018 | Li |
| 9,956,227 B2 | 5/2018 | Vanover et al. |
| 10,010,553 B2 | 7/2018 | Fienberg et al. |
| 10,011,602 B2 | 7/2018 | Kjer-Nielsen et al. |
| 10,072,010 B2 | 9/2018 | Li et al. |
| 2001/0008942 A1 | 7/2001 | Buchwald et al. |
| 2003/0069246 A1 | 4/2003 | Darrow et al. |
| 2003/0092908 A1 | 5/2003 | Pitts et al. |
| 2003/0162782 A1 | 8/2003 | Grossman et al. |
| 2003/0211040 A1 | 11/2003 | Greengard et al. |
| 2004/0034015 A1 | 2/2004 | Robichaud et al. |
| 2004/0087517 A1 | 5/2004 | Burnet et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2005/0075795 A1 | 4/2005 | Pandit et al. |
| 2005/0113379 A1 | 5/2005 | Ge et al. |
| 2005/0166771 A1 | 8/2005 | Gygi et al. |
| 2005/0222209 A1 | 10/2005 | Zeldis et al. |
| 2006/0041014 A1 | 2/2006 | Naylor et al. |
| 2006/0205787 A1 | 9/2006 | Muller et al. |
| 2007/0082929 A1 | 4/2007 | Gant et al. |
| 2007/0197695 A1 | 8/2007 | Potyen et al. |
| 2008/0069885 A1 | 3/2008 | Mesens et al. |
| 2008/0096870 A1 | 4/2008 | Martynyuk et al. |
| 2008/0132552 A1 | 6/2008 | Kleinman et al. |
| 2008/0176961 A1 | 7/2008 | Greengard et al. |
| 2008/0193964 A1 | 8/2008 | Greengard et al. |
| 2008/0194592 A1 | 8/2008 | Mates et al. |
| 2008/0280941 A1 | 11/2008 | Lourtie |
| 2010/0087450 A1 | 4/2010 | Mates et al. |
| 2010/0173878 A1 | 7/2010 | Li et al. |
| 2010/0273753 A1 | 10/2010 | Li et al. |
| 2010/0323997 A1 | 12/2010 | Fienberg et al. |
| 2011/0190373 A1 | 8/2011 | Yan et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0070443 A1 | 3/2012 | Movsesian |
| 2012/0071450 A1 | 3/2012 | Li et al. |
| 2012/0094966 A1 | 4/2012 | Li et al. |
| 2012/0136013 A1 | 5/2012 | Li et al. |
| 2013/0239234 A1 | 9/2013 | Greengard et al. |

(56) References Cited

U.S. PATENT DOCUMENTS

| | | | |
|---|---|---|---|
| 2014/0005155 A1 | 1/2014 | Li et al. |
| 2014/0011783 A1 | 1/2014 | Li et al. |
| 2014/0080816 A1 | 3/2014 | Koolman et al. |
| 2014/0148421 A1 | 5/2014 | Li et al. |
| 2014/0194396 A1 | 7/2014 | Li et al. |
| 2014/0315868 A1 | 10/2014 | Li et al. |
| 2015/0038474 A1 | 2/2015 | Li et al. |
| 2015/0072964 A1 | 3/2015 | Mates et al. |
| 2015/0072965 A1 | 3/2015 | Li et al. |
| 2015/0080357 A1 | 3/2015 | Li et al. |
| 2015/0080404 A1 | 3/2015 | Mates et al. |
| 2015/0197524 A1 | 7/2015 | Li et al. |
| 2015/0197528 A1 | 7/2015 | Li et al. |
| 2015/0353556 A1 | 12/2015 | Li et al. |
| 2016/0031895 A1 | 2/2016 | Li et al. |
| 2016/0038494 A1 | 2/2016 | Wennogle et al. |
| 2016/0039835 A1 | 2/2016 | Li et al. |
| 2016/0083390 A1 | 3/2016 | Li et al. |
| 2016/0354315 A1 | 12/2016 | Li |
| 2017/0114037 A1 | 4/2017 | Davis et al. |
| 2017/0183350 A1 | 6/2017 | Mates et al. |
| 2017/0189398 A1 | 7/2017 | Mates et al. |
| 2017/0226117 A1 | 8/2017 | Li et al. |
| 2017/0319580 A1 | 11/2017 | Yao et al. |
| 2018/0000825 A1 | 1/2018 | Wennogle et al. |

FOREIGN PATENT DOCUMENTS

| | | |
|---|---|---|
| EP | 0058481 | 8/1982 |
| EP | 0063381 | 10/1982 |
| EP | 0095289 | 11/1983 |
| EP | 0136883 | 4/1985 |
| EP | 0201188 | 12/1986 |
| EP | 0274234 | 7/1988 |
| EP | 0358398 | 3/1990 |
| EP | 0509442 | 10/1992 |
| EP | 0519738 | 12/1992 |
| EP | 0599444 | 6/1994 |
| EP | 0636626 | 2/1995 |
| EP | 0690070 | 1/1996 |
| EP | 0733642 | 9/1996 |
| EP | 0830863 | 3/1998 |
| EP | 0856508 | 8/1998 |
| EP | 0976732 | 2/2000 |
| EP | 1097719 | 5/2001 |
| EP | 0911333 | 4/2002 |
| EP | 1245553 | 10/2002 |
| EP | 1254884 | 11/2002 |
| EP | 1564671 | 8/2005 |
| GB | 1476087 | 6/1977 |
| GB | 2145422 | 3/1985 |
| JP | 53031694 | 3/1978 |
| JP | 2008545783 | 12/2008 |
| JP | 2011506321 | 3/2011 |
| KR | 10-1991-0006866 | 9/1991 |
| WO | WO 1991/009840 | 7/1991 |
| WO | WO 1991/019717 | 12/1991 |
| WO | WO 1993/009101 | 5/1993 |
| WO | WO 1994/015908 | 7/1994 |
| WO | WO 1994/019351 | 9/1994 |
| WO | WO 1994/024125 | 10/1994 |
| WO | WO 1995/013814 | 5/1995 |
| WO | WO 1996/014293 | 5/1996 |
| WO | WO 1998/015515 | 4/1998 |
| WO | WO 1998/043956 | 10/1998 |
| WO | WO 1998/046606 | 10/1998 |
| WO | WO 1998/052568 | 11/1998 |
| WO | WO 1999/043643 | 9/1999 |
| WO | WO 2000/002887 | 1/2000 |
| WO | WO 2000/035419 | 6/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2001/027113 | 4/2001 |
| WO | WO 2002/059129 | 8/2002 |
| WO | WO 2002/074312 | 9/2002 |
| WO | WO 2002/085838 | 10/2002 |
| WO | WO 2003/002567 | 1/2003 |
| WO | WO 2003/014118 | 2/2003 |
| WO | WO 2003/020702 | 3/2003 |
| WO | WO 2003/020724 | 3/2003 |
| WO | WO 2003/042216 | 5/2003 |
| WO | WO 2003/093499 | 11/2003 |
| WO | WO 2004/010981 | 2/2004 |
| WO | WO 2004/013094 | 2/2004 |
| WO | WO 2004/031375 | 4/2004 |
| WO | WO 2004/039788 | 5/2004 |
| WO | WO 2004/056324 | 7/2004 |
| WO | WO 2004/081563 | 9/2004 |
| WO | WO 2006/034187 | 3/2006 |
| WO | WO 2006/081251 | 8/2006 |
| WO | WO 2006/133261 | 12/2006 |
| WO | WO 2007/025103 | 3/2007 |
| WO | WO 2007/084841 | 7/2007 |
| WO | WO 2007/143568 | 12/2007 |
| WO | WO 2007/143705 | 12/2007 |
| WO | WO 2008/063505 | 5/2008 |
| WO | WO 2008/070095 | 6/2008 |
| WO | WO 2008/112280 | 9/2008 |
| WO | WO 2009/017836 | 2/2009 |
| WO | WO 2009/073210 | 6/2009 |
| WO | WO 2009/075784 | 6/2009 |
| WO | WO 2009/114181 | 9/2009 |
| WO | WO 2009/137465 | 11/2009 |
| WO | WO 2009/145900 | 12/2009 |
| WO | WO 2010/065147 | 6/2010 |
| WO | WO 2010/065148 | 6/2010 |
| WO | WO 2010/065149 | 6/2010 |
| WO | WO 2010/065151 | 6/2010 |
| WO | WO 2010/065152 | 6/2010 |
| WO | WO 2010/065153 | 6/2010 |
| WO | WO 2010/065617 | 6/2010 |
| WO | WO 2010/098839 | 9/2010 |
| WO | WO 2011/016861 | 2/2011 |
| WO | WO 2011/043816 | 4/2011 |
| WO | WO 2011/133224 | 10/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |
| WO | WO 2012/171016 | 12/2012 |
| WO | WO 2013/024164 | 2/2013 |
| WO | WO 2013/155504 | 10/2013 |
| WO | WO 2013/155505 | 10/2013 |
| WO | WO 2013/155506 | 10/2013 |
| WO | WO 2013/192556 | 12/2013 |
| WO | WO 2014/127331 | 8/2014 |
| WO | WO 2014/145192 | 9/2014 |
| WO | WO 2014/145617 | 9/2014 |
| WO | WO 2014/151409 | 9/2014 |
| WO | WO 2015/085004 | 6/2015 |
| WO | WO 2015/154025 | 10/2015 |
| WO | WO 2015/154030 | 10/2015 |
| WO | WO 2015/191554 | 12/2015 |
| WO | WO 2016/022893 | 2/2016 |
| WO | WO 2017/132408 | 8/2017 |
| WO | WO 2017/165755 | 9/2017 |
| WO | WO 2017/165843 | 9/2017 |

OTHER PUBLICATIONS

Angst, J., et al., "Prevalence and Characteristics of Undiagnosed Bipolar Disorders in Patients With a Major Depressive Episode," Arch. Gen. Psychiatry, 68(8): 701-709 (2011).

"Anxiety," [retrieved on Aug. 1, 2018]. Retrieved online via Internet, 5 pages, URL: <http://www.nlm.nih.gov/medlineplus/anxiety.html>.

Aswar, "Anti-Cataleptic Activity of Various Extracts of Ocimum Sanctum," International Journal of Pharma Research and Development, 2(6): 1-7 (2010).

"Autism," [retrieved on Aug. 1, 2018]. Retrieved online via Internet, 6 pages, URL: <http://www.nlm.nih.gov/medlineplus/autism.html>.

(56) References Cited

OTHER PUBLICATIONS

Avendaño, C., et al., "The Problem of the Existence of C(Ar)—H . . . N Intramolecular Hydrogen Bonds in a Family of 9-Azaphenyl-9H-carbazoles," J. Chem. Soc. Perkin. Trans., 2: 1547-1555 (1993).
Baillie, T.A., "The Use of Stable Isotopes in Pharmacological Research," Pharmacological Reviews, 33(2): 81-132 (1981).
Balbach, S., et al., "Pharmaceutical evaluation of early development candidates 'the 100 mg-approach,'" International Journal of Pharmaceutics, 275: 1-12 (2004).
Banker, Gilbert S., et al., Modern Pharmaceutics, Marcel Dekker, New York, 1996.
Bastia, E., et al., "Effect of A1 and A2A Adenosine Receptor Ligands in Mouse Acute Models of Pain," Neuroscience Letters, 328: 241-244 (2002).
Bastin, R., et al., "Salt Selection and Optimisation Procedures for Pharmaceutical New Chemical Entities," Organic Process Research & Development, 4: 427-435 (2000).
Beletskaya, I., et al., "Pd- and Cu-catalyzed selective Arylation of Benzotriazole," Tetrahedron Letters, 39: 5617-5620 (1998).
Bender, A.T., et al., "Cyclic Nucleotide Phosphodiesterases: Molecular Regulation to Clinical Use," Pharmacological Reviews, 58(3): 488-520 (2006).
Bender, et al., "Selective up-regulation of PDE1B2 upon monocyte-to-macrophage differentiation," PNAS, 102(2): 497-502 (2005).
Bennett, J.C., "Cecil Textbook of Medicine," 20th Edition, vol. 1, 1004-1010 (1996).
Berger, J., et al., "Synthesis of Some Conformationally Restricted Analogues of Fentanyl," Journal of Medicinal Chemistry, 20(4): 600-602 (1977).
Blokland, A., et al., "PDE Inhibition and Cognition Enhancement," 22(4): 349-354 (2012) (abstract only).
Boger, D., et al., "Inverse Electron Demand Diels-Alder Reactions of Heterocyclic Aza Dienes. Studies on the Total Synthesis of Lavendamycin: Investigative Studies on the Preparation of the CDE β-Carboline Ring System and AB Quinoline-5, 8-quinone Ring System," J. Org. Chem., 50: 5782-5789 (1985).
Borhans, B., et al., "Animal models for posttraumatic stress disorder: An overview of what is used in research," World J. Psychiatr., 5(4): 387-396 (2015).
Bowman, W.R., et al., "Copper(1) Catalysed Aromatic Nucleophilic Substitution: A Mechanistic and Synthetic Comparison with the SRN1 Reaction," Tetrahedron Letters, 25(50): 5821-5824 (1984).
Bowman, W.R., et al., "Intramolecular Aromatic Substitution (SRN1) Reactions, Use of Entrainment for the Preparation of Benzothiazoles," Tetrahedron Letters, 23(48): 5093-5096 (1982).
Bowman, W.R., et al., "Synthesis of 1H-quinazoline-4-ones using intramolecular aromatic nucleophilic substitution," ARKIVOC, x: 434-442 (2003).
Boyd, et al., "Dopamine receptor signaling and current and future antipsychotic drugs," Handbook Exp. Pharmacol., 212: 53-86 (2012).
Bremner, J.D., "Neuroimaging of Posttraumatic Stress Disorder," Psychiatric Annals, 28(8): 445-450 (1998).
Browne, T.R., "Stable Isotope Techniques in Early Drug Development: An Economic Evaluation," J. Clin. Pharmacol., 38: 213-220 (1998).
Bryan-Lluka, L., et al., "Potencies of haloperidol metabolites as inhibitors of the human noradrenaline, dopamine and serotonin transporters in transfected COS-7 cells," Naunyn-Shemiedeberg's Arch Pharmacol., 360: 109-115 (1999).
Burger, A., "Isoterism and Bioisoterism in Drug Design," Progress in Drug Research, 37: 287-328 (1991).
Burnouf, C., et al., "Synthesis, Structure-Activity Relationships, and Pharmacological Profile of 9-Amino-4-oxo-1-phenyl-3,4,6,7-tetrahydro[1,4]diazepino[6,7,1-hi]indoles: Discovery of Potent, selective Phosphodiesterase Type 4 inhibitors," Journal of Medicinal Chemistry, 43(25): 4850-4867 (2000).
Byrn, S., et al., "Pharmaceutical Solids: A Strategic Approach to Regulatory Considerations," Pharmaceutical Research, 12(7): 945-954 (1995).

Caira, M.R., "Crystalline Polymorphism of Organic Compounds," Topics in Current Chemistry, 198: 163-203 (1998).
Chalimoniuk, "Upregulation of guanylyl cyclase expression and activity in striatum of MPTP-induced parkinsonism in mice," Biochem. Biophys. Res. Commun., 324(1): 118-126 (2004).
Chebib, M., et al., "1-Phenylpyrazolo[3,4-d]pyrimidines; Structure-Activity in Relationships for C6 Substituents at A1 and A2A Adenosine Receptors," Bioorganic & Medicinal Chemistry, 8: 2581-2590 (2000).
Chen, et al., "Broad Spectrum neuroprotection profile of phosphodiesterase inhibitors as related to modulation of cell-cucle elements and caspase-3 activation," Neuroscience Letters, 418: 165-169 (2007).
Chen, M., et al., "Effects of Bimatoprost 0.03% on Ocular Hemodynamics in Normal Tension Glaucoma," Journal of Ocular Pharmacology and Therapeutics, 22(3): 188-193 (2006).
Chermat, R., et al., "Adaptation of the Tail Suspension Test to the Rat," Journal de Pharmacologie (Paris), 17(3): 348-350 (1986).
Cherrah, Y., et al., "Study of Deuterium Isotope Effects on Protein Binding by Gas Chromatography/Mass Spectrometry, Caffeine and Deuterated Isotopomers," Biomedical and Environmental Mass Spectrometry, 14: 653-657 (1987).
Crawford, K., et al., "Copper-catalyzed amidations of bromo substituted furans and thiophenes," Tetrahedron Letters, 43: 7365-7368 (2002).
Cristina, R.T., et al., "Pharmacologic Activity of Phosphodiesterases and their Inhibitors," Lucrari Stiintifice Medicina Veterinara, XLIII(2): 300-314 (2010).
Cullen, K.R., et al., "Atypical Antipsychotics for Treatment of Schizophrenia Spectrum Disorders," Mar. 1, 2008, 7 pages, URL: <http://www.psychiatrictimes.com/schizophrenia/atypical-antipsychotics-treatment-schizophrenia-spectrum-disorders/page/0/2>.
Darmani, N., et al., "Do Functional Relationships Exist Between 5-HT1A and 5-HT2 Receptors?" Pharmacology Biochemistry & Behavior, 36: 901-906 (1990).
Daviglus, et al., "National Institutes of Health State-of-the-Science Conference Statement: Preventing Alzheimer Disease and Cognitive Decline," Annals of Internal Medicine, 153(3): 176-185 (2010).
Davis, R., et al., "ITI-007 demonstrates brain occupancy at serotonin 5-HT2A and dopamine D2 receptors and serotonin transporters using positron emission tomography in healthy volunteers," Psychopharmacology, Published Online Apr. 7, 2015, pp. 1-10.
Davis, R., et al., "ITI-007 in the treatment of schizophrenia: from novel pharmacology to clinical outcomes," Expert Review of Neurotherapeutics, 16(6): 601-614 (2016).
DE19931206, Steif, "Relaxing, or increasing cyclic adenosine monophosphate concenctration in smooth muscular tissue, e.g. by administration of cAMP phosphodiesterase inhibitors, dipyridamole or sildenafil," Jan. 11, 2001, English language machine translation of abstract, Espacenet, date obtained: Aug. 1, 2018, 2 pages: <URL: https://worldwide.espacenet.com/publicationDetails/biblio?CC=DE&NR=19931206A1&KC=A1&FT=D&ND=3&date=20010111&DB=&locale=en_EP>.
DE102005042877, Bayer Healthcare AG, "Use of PDE1A polypeptides, or nucleic acid, for identifying their specific inhibitors, which are useful for treatment and prevention of cardiac insufficiency," Mar. 22, 2007, English language machine translation of abstract, Espacenet, date obtained: Nov. 15, 2016, 1 page: <URL: https://worldwide.espacenet.com/publicationDetails/biblio?CC=DE&N>.
Deshmukh, et al., "Amelioration of intracerebroventricular streptozotocin induced cognitive dysfunction and oxidative stress by vinpocetine—a PDE1 inhibitor," European Journal of Pharmacology, 620(1-3): 49-56 (2009).
Dewald, et al., "Synthesis and Potential Antipsychotic Activity of 1 H-Imidazo[1.2-c]pyrazolo[3,4-e]pyrimidines," J. Med. Chem., 31: 454-461 (1988).
Dyck, L.E., et al., "Effects of Deuterium Substitution on the Catabolism of B-Phenylethylamine: An In Vivo Study," Journal of Neurochemistry, 46(2): 399-404 (1986).
Ehrman, et al., "Phosphodiesterase 1B differentially modulates the effects of methamphetamine on locomotor activity and spatial

(56) References Cited

OTHER PUBLICATIONS learning through DARPP32-dependent pathways: evidence from PDE1B-DARPP32 double-knockout mice," Genes Brain Behav., 5(7): 540-551 (2006).
Ennaceur, A., et al., "A New On-Trial Test for Neurobiologicla Studies of Memory in Rats, 1: Behavioral Data," Behavioural Brain Research, 31: 47-59 (1988).
EP0063381, Byk Gulden Lomberg Chem Fab, "Pyrazolo(3-4-d) pyrimidines, process for their preparation and pharmaceutical compositions containing them," Oct. 27, 1982, English language machine translation of abstract, Espacenet, date obtained: Dec. 28, 2018, 1 page: <URL: https://worldwide.espacenet.com/publicationDetails/biblio?CC=EP&N>.
EP0733642, Kali Chemie Pharma GMBH, "Benzazepin-, benzoxazepin- and benzothiazepin-N-acetic acid-derivatives, their preparation and their pharmaceutical compositions," Sep. 25, 1996, English language machine translation of abstract, Espacenet, date obtained: Dec. 28, 2018, 1 page: <URL: https://worldwide.espacenet.com/publicationDetails/biblio?CC=EP&N>.
EP0830863, Solvay Pharm GMBH, "Drugs for increasing gastrointestinal blood supply," Mar. 25, 1998, English language machine translation of abstract, Espacenet, date obtained: Dec. 28, 2018, 1 page: <URL: https://worldwide.espacenet.com/publicationDetails/biblio?CC=EP&N>.
Evgenov, et al., "Inhibition of phosphodiesterase 1 augments the pulmonary vasodilator response to inhaled nitric oxide in awake lambs with acute pulmonary hypertension," Am. J. Physiol. Lung Cell Mol Physiol., 290: L723-L729 (2006).
Evindar, G., et al., "Copper- and Palladium-Catalyzed Intramolecular Aryl Guanidinylation: An Efficient Method for the Synthesis of 2-Aminobenzimidazoles," Organic Letters, 5(2): 133-136 (2003).
Eyles, D., et al., "Stereospecific Reduction of Haloperidol in Human Tissues," Biochemical Pharmacology, 44(5): 867-871 (1992).
Ezquerra, J., et al., "Efficient Reagents for the Synthesis of 5-, 7-, and 5,7-Substituted Indoles Starting from Aromatic Amines. Scope and Limitations," J. Org. Chem., 61: 5804-5812 (1996).
Fawcett, J., "Posttraumatic Stress Disorder, Stress, and Happiness," Psychiatric Annals, 28(8): 427-428 (1998).
Fee, W.W., et al., "Copper(II)—Promoted Solvolyses of Nickel(II) Complexes III. Tetradentate Schiff Base Ligands Containing Various Diamine Segments," Aust. J. Chem., 26: 1475-1485 (1973).
Ferreira, I., et al., "Novel synthetic routes to thienocarbazoles via palladium or copper catalyzed amination or amidation of arylhalides and intramolecular cyclization," Tetrahedron, 58: 7943-7949 (2002).
Fienberg, et al., "DARPP-32: Regulator of the Efficacy of Dopaminergic Neurotransmission," Science, 281: 838-842 (1998).
Filgueiras, et al., "Phosphodiesterase type 1 inhibition improves learning in rats exposed to alcohol during the third trimester equivalent of human gestation," Neuroscience Letters, 473(3): 202-207 (2010).
Finet, J., et al., "Recent Advances in Ullmann Reaction: Copper(II) Diacetate Catalysed N-, O- and S-Arylation Involving Polycoordinate Heteroatomic Derivatives," Current Organic Chemistry, 6: 597-626 (2002).
Fitzgerald, R.J., et al., "Inhibition of Caries in Hamsters by 2-Deoxy-D-Glucose," J. Dent. Res., 56(11): 1431 (1977).
Foster, P., et al., "Acetylcholinesterase inhibitors reduce spreading activation in dementia," Neuropsychologia, 50: 2093-2099 (2012).
Foster, A.B., "Deuterium Isotope Effects in the Metabolism of Drugs and Xenobiotics: Implications for Drug Design," Advances in Drug Research, Academic Press, London, G.B., (1985).
Friedman, M.J., "Current and Future Drug Treatment for Posttraumatic Stress Disorder Patients," Psychiatric Annals, 28(8): 464-468 (1998).
Gelbin, M., et al., "Ketene-S,N-acetals as synthons for heterocycles, new synthesis of pyrimidinones," Journal Fur Praktische Chemie, 329(5): 753-766 (1987).
Ghorab, M., et al., "Synthesis, Anticancer and Radioprotective Activities of Some New Pyrazolo[3,4-d]pyrimidines Containing Amino Acid Moieties," Arzneimittelforschung, 59(2): 96-103 (2009).

Ghosh, R., et al., "Phosphodiesterase Inhibitors: Their Role and Implications," Int. J. of Pharm. Tech. Research, 1(4): 1148-1160 (2009).
Giachini, et al., "CHBPR: Decreased cGMP level contributes to increased contraction in arteries from hypertensive rats: role of PDE1," Hypertension, 57(3): 655-663 (2011).
Goldman-Rakic, P., et al., "Targeting the Dopamine D1 Receptor in Schizophrenia: Insights for Cognitive Dysfunction," Psychopharmacology, 174: 3-16 (2004).
Goodbrand, H.B., et al., "Ligand-Accelerated Catalysis of the Ullmann Condensation: Application to Hole Conducting Triarylamines," J. Org. Chem., 64: 670-674 (1999).
Goodman & Gilman, Las bases farmacólogicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.
Gouyette, A., "Synthesis of Deuterium-labelled Elliptinium and its Use in Metabolic Studies," Biomedical and Environmental Mass Spectrometry, 15: 243-247 (1988).
Grant, "Polymorphism in Pharmaceutical Solids," Chapter 1, 1-10 (1999).
Greengard, et al., "Beyond the Dopamine Receptor: the DARPP-32 Protein Phosphotase-1 Cascade," Neuron, 23: 435-447 (1999).
Guillory, "Polymorphism in Pharmaceutical Solids," Chapter 5, 183-226 (1999).
Gulyas, B., et al., "PET studies on the brain uptake and regional distribution of [11C]vinpocetine in human subjects," Acta Neurologica Scandinavica, 106: 35-332 (2002).
Hackam, D., et al., "Translation of Research Evidence from Animals to Humans," JAMA, 296(14): 1731-1732 (2006).
Halene, et al., "Antipsychotic-Like Properties of Phosphodiesterase 4 Inhibitors: Evaluation of 4-(3-Butoxy-4-methoxybenzyl)-2-imidazolidinone (RO-20-1724) with Auditory Event-Related Potentials and Prepulse Inhibition of Startle," J. Pharmacol. Exp. Ther., 326(1): 230-239 (2008).
Hall, et al., "Autoradiographic evaluation of [11C]vinpocetine Binding in the Human Postmortem Brain," Acta Biologica Hungarica, 53(1-2): 59-66 (2002).
Hamann, B., et al., "Systematic Variation of Bidentate Ligands Used in Aryl Halide Amination. Unexpected Effects of Steric, Electronic, and Geometric Perturbations," J. Am. Chem. Soc., 120: 3694-3703 (1998).
Han, et al., "The Calcium/Calmodulin-dependent Phosphodiesterase PDE1C Downregulates Glucose-induced Insulin Secretion," J. Bio. Chem., 274(32): 22337-22344 (1999).
Harbert, C., et al., "Neuroleptic Activity in 5-Aryltetrahydro-γ-carbolines," J. Med. Chem., 23: 635-643 (1980).
Hartwig, J.F., "Palladium-Catalyzed Amination of Aryl Halides: Mechanism and Rational Catalyst Design," Synlett, 329-340 (1996).
Harvey, B., et al., "Serotonin and Stress: Protective or Malevolent Actions in the Biobehavioral Response to Repeated Trauma?" Annals of the New York Academy of Sciences, 1032: 267-272 (2004).
Haskins, N.J., "The Application of Stable Isotopes in Biomedical Research," Biomedical Mass Spectrometry, 9(7): 269-277 (1982).
Hassan, J., et al., "Aryl-aryl bond formation one century after the discovery of the ullmann reaction," Chem. Rev., 102: 1359-1469 (2002).
Haynes, D., "Occurrence of Pharmaceutically Acceptable Anions and Cations in the Cambridge Structural Database," Journal of Pharmaceutical Sciences, 94(10): 2111-2120 (2005).
Honma, S., "The Metabolism of Roxatidine Acetate Hydrochloride: Liberation of Deuterium from the Piperidine Ring during Hydroxylation," Drug Metabolism and Disposition, 15(4): 551-559 (1987).
Hulley, et al., "Cyclic AMP promotes the survival of dopaminergic neurons in vitro and protects them from the toxic effects of MPP+," J. Neural Transm. Suppl., 46: 217-228 (1995).
International Search Report for International Application No. PCT/US2006/022066, dated Apr. 3, 2007, 2 pages.
International Search Report for International Application No. PCT/US2008/003340, dated Aug. 8, 2008, 3 pages.

(56) References Cited

OTHER PUBLICATIONS

International Search Report for International Application No. PCT/US2009/001608, dated Apr. 27, 2009, 2 pages.
International Search Report for International Application No. PCT/US2009/003261, dated Jul. 16, 2009, 3 pages.
International Search Report for International Application No. PCT/US2011/000719, dated Jul. 5, 2011, 3 pages.
International Search Report for International Application No. PCT/US2013/036512, dated Aug. 19, 2013, 4 pages.
International Search Report for International Application No. PCT/US2013/036514, dated Aug. 16, 2013, 3 pages.
International Search Report for International Application No. PCT/US2013/036515, dated Aug. 13, 2013, 3 pages.
International Search Report for International Application No. PCT/US2014/016741, dated May 14, 2014, 3 pages.
International Search Report for International Application No. PCT/US2014/025666, dated Jul. 7, 2014, 3 pages.
International Search Report for International Application No. PCT/US2014/030412, dated Nov. 6, 2014, 4 pages.
International Search Report for International Application No. PCT/US2015/036890, dated Sep. 14, 2015, 4 pages.
International Search Report for International Application No. PCT/US2015/044164, dated Oct. 29, 2015, 3 pages.
International Search Report for International Application No. PCT/US2017/024575, dated Jun. 20, 2017, 3 pages.
Ito, T., et al., "Studies of Organic Catalytic Reactions. VI. The Function of Pyridine and Copper in the Rosenmund-von Braun Reaction," Bulletin of the Chemical Society of Japan, 41: 419-423 (1968).
Izrayelit, L., "Schizoaffective Disorder and PTSD Successfully Treated With Olanzapine and Supportive Psychotherapy," Psychiatric Annals, 28(8): 424-426 (1998).
Jain, N.K., et al., "Polymorphism in Pharmacy," Indian Drugs, 23(6): 315-316 (1986).
Javitt, D.C., et al., "Recent Advances in the Phencyclidine Model of Schizophrenia," Am. J. Psychiatry, 148(10): 1301-1308 (1991) (abstract only).
Ji, H-M., et al., "Efficacy of vinpocetine on neuropathy in patients with type 2 diabetes mellitus," Chinese Journal of New Drugs, 18(15), (2009) (abstract only).
Ji, J., "Selective Amination of Polyhalpyridines Catalyzed by a Palladium-Xantphos Complex," Organic Letters, 5(24): 4611-4614 (2003).
Jiang, et al., "Chemoenzymatic Asymmetric Total Synthesis of Phosphodiesterase Inhibitors: Preparation of a Polycyclic Pyrazolo[3,4-d]pyrimidine from an Acylnitroso Oiels-Alder Cycloadduct-Derived Aminocyclopentenol," J. Org. Chem., 70: 2824-2827 (2004).
Jordan, V.C., "Tamoxifen: A Most Unlikely Pioneering Medicine," Nature Reviews: Drug Discovery, 2: 205-213 (2003).
JP53031694A, Takeda Chem Ind Ltd., "3-Aminopyrazolo(3,4-)pyrimidine derivatives and their preparation," Mar. 25, 1978, English language abstract, 1 page.
Kakkar, et al., "Amantadine: an antiparkinsonian agent inhibits bovine brain 60 kDa calmodulin-dependent cyclic nucleotide phosphodiesterase isozyme," Brain Res., 749(2): 290-294 (1997).
Kakkar, et al., "Calmodulin-dependent cyclic nucleotide phosphodiesterase in an experimental rat model of cardiac ischemia-reperfusion," Can J Physiol Pharmacol., 80(1): 59-66 (2002) (abstract only).
Kakkar, et al., "Calmodulin-dependent cyclic nucleotide phosphodiesterase (PDE1)," Cell Mol Life Sci., 55(8-9): 1164-1186 (1999).
Kakkar, et al., "Inhibition of Bovine Brain Calmodulin-Dependent Cyclic Nucleotide Phosphodiesterase Isozymes by Deprenyl," Life Sciences, 59(21): 337-341 (1996).
Kametani, T., et al., "A Novel Synthesis of Indole Derivatives," Heterocycles, 14(3): 277-280 (1980).
Kang, S.K., "Copper-catalyzed N-Arylation of Aryl Iodides with Benzamides or Nitrogen Heterocycles in the Presence of Ethylenediamine," Synlett, 3: 427-430 (2002).

Kay, S., et al., "The Positive and Negative Syndrome Scale (PANSS) for Schizophrenia," Schizophrenia Bulletin, 13(2): 261-276 (1987).
Kessler, R., et al., "Lifetime Prevalence and Age-of-Onset Distributions of DSM-IV Disorders in the National Comorbidity Survey Replication," Arch. Gen. Psychiatry, 62: 593-602 (2005).
Khorana, N., et al., "Y-Carbolines: Binding at 5-HT5A Serotonin Receptors," Bioorganic & Medicinal Chemistry, 11: 717-722 (2003).
Kim, et al., "Upregulation of Phosphodiesterase 1A1 Expression is Associated with the Development of Nitrate Tolerance," Circulation, 104(19): 2338-2343 (2001).
Kiyomori, A., et al., "An Efficient Copper-Catalyzed Coupling of Aryl Halides with Imidazoles," Tetrahedron Letters, 40: 2657-2660 (1999).
Klaissle, "Physical activity and environmental enrichment regulate the generation of neural precursors in the adult mouse substantia nigra in a dopamine-dependent manner," BMC Neurosci., (2012).
Klapars, A., et al., "A General and Efficient Copper Catalyst for the Amidation of Aryl Halides," J. Am. Chem. Soc., 124: 7421-7428 (2002).
Klapars, A., et al., "A General and Efficient Copper Catalyst for the Amidation of Aryl Halides and the N-Arylation of Nitrogen Heterocycles," J. Am. Chem. Soc., 123: 7727-7729 (2001).
Kleppisch, "Phosphodiesterases in the central nervous system," Handb. Exp. Pharmacol., 191: 71-92 (2009).
Kondratov, S.A., et al., "Nucleophilic Substitution in the Aromatic Series. LV. Reaction of o-Nitrochlorobenzene with Ammonia in the Presence of Copper Compounds," Zhurnal Organidreskoi Khimii, 51(11): 2387-2390 (1979).
Koppel, J., et al., "Optimal treatment of Alzheimer's disease psychosis: challenges and solutions," Neuropsychiatric Disease and Treatment, 10: 2253-2262 (2014).
Kotera, et al., "Recent progress in cyclic nucleotide phosphodiesterase research: isozymes, functions, and inhibitors," Folia Pharmacol. Jpn., 126(2): 121-127 (Japanese translation only—no English translation available).
Kwong, F., et al., "Mild and Efficient Copper-Catalyzed Amination of Aryl Bromides with Primary Alkylamines," Organic Letters, 5(6): 793-796 (2003).
Laddha, et al., "A new therapeutic approach in Parkinson's disease: some novel quinazoline derivatives as dual selective phosphodiesterase 1 inhibitors and anti-inflammatory agents," Bioorganic & Medicinal Chemistry, 17(19): 6796-6802 (2009).
Lebert, F., et al., "Trazodone in Fronto-Temporal Dementia," Research and Practice in Alzheimer's Disease, 11: 356-360 (2006).
Lee, T., et al., "Novel, Highly Potent, Selective 5-HT2A/D2 Receptor Antagonists as Potential Atypical Antipsychotics," Bioorganic & Medicinal Chemistry Letters, 13: 767-770 (2003).
Li, P., et al., "Discovery of a Tetracyclic Quinoxaline Derivative as a Potent and Orally Active Multifunctional Drug Candidate for the Treatment of Neuropsychiatric and Neurological Disorders," Journal of Medicinal Chemistry, 57(6): 2670-2682 (2014).
Lieberman, J., et al., "ITI-007 for the Treatment of Schizophrenia: A 4-Week Randomized, Double-Blind, Controlled Trial," Biol. Psychiatry, 79(12): 952-961 (2015).
Lin, Y., et al., "Dosage and duration of antipsychotic treatment in demented outpatients with agitation or psychosis," Journal of the Formosan Medical Association, 114: 147-153 (2015).
Lipschitz, D., et al., "Childhood Posttraumatic Stress Disorder: A Review of Neurobiologic Sequelae," Psychiatric Annals, 28(8): 452-457 (1998).
Lopez, O., et al., "Psychiatric Symptoms Vary With the Severity of Dementia in Probable Alzheimer's Disease," J. Neuropsychiatry Clin. Neurosci., 15(3): 346-353 (2003).
Louie, J., et al., "Palladium-Catalyzed Synthesis of Arylamines from Aryl Halides Mechanistic Studies Lead to Coupling in the Absence of Tin Reagents," Tetrahedron Letters, 36(21): 3609-3612 (1995).
Lounkine, E., et al., "Formal Concept Analysis for the Identification of Molecular Fragment Combinations Specific for Active and Highly Potent Compounds," J. Med. Chem., 51: 5342-5348 (2008).

(56) References Cited

OTHER PUBLICATIONS

Lourenco, et al., "Characterization of R-[11C]rolipram for PET imaging of phosphodiesterase-4; in vivo binding, metabolism, and dosimetry studies in rats," Nuclear Medicine and Biology, 28: 347-358 (2001).
Lundbeck Poster Presentation: Kehler, J., et al., "344—Discovery of the Brain Penetrant Phosphodiesterase 1 (PDE1) Inhibitor Lu AF64386," 253rd American Chemical Society National Meeting, San Francisco, (2017) (abstract only).
Lundbeck Poster Presentation: Mork, A., et al., "429.2 / UU83—The Phosphodiesterase 1 Inhibitor Lu AF64386 Increases cGMP and cAMP in the Brain and Exerts Procognitive Effects in the Rat," Society for Neuroscience Meeting, Session 429—Learning and Memory: Pharmacology (2017) (abstract only).
Lundqvist, T., et al., "Exploitation of Structural and Regulatory Diversity in Glutamate Racemases," Nature, 447: 817-822 (2007).
Madhusoodanan, S., et al., "Pharmacological management of behavioral symptoms associated with dementia," World Journal of Psychiatry, 4(4): 72-79 (2014).
Mani, S.K., et al., "Requirement for DARPP-32 in Progesterone-Facilitated Sexual Receptivity in Female Rats and Mice," Science, 287: 1053-1056 (2000).
March, et al., Advanced Organic Chemistry; Reactions, Mechanisms, and Structures, Fourth Edition, 910-911 (1992).
Marcoux, J., et al., "A General Copper-Catalyzed Synthesis of Diaryl Ethers," J. Am. Chem. Soc., 119: 10539-10540 (1997).
Marek, G.J., et al., "Synergistic Action of 5-HT2A Antagonists and Selective Serotonin Reuptake Inhibitors in Neuropsychiatric Disorders," Neuropsychopharmacology, 28: 402-412 (2003).
Medina, "Therapeutic Utility of Phosphodiesterase Type 1 Inhibitors in Neurological Conditions," Front. Neurosci., 5(21), 6 pages (2011).
Miller, et al., "Cyclic nucleotide phoshpodiesterase 1A: a key regulator of cardiac fibroblast activation and extracellular matrix remodeling in the heart," Basic Res. Cardiol., 106(6): 1023-1039 (2011).
Miller, et al., "Role of Ca2+/calmdoulin-stimulated cyclic nucleotide phosphodiestearse 1 in mediating cardiomyocyte hypertrophy," Circ. Res., 105(10): 956-964 (2009).
Mohamed, S., et al., "Pharmacotherapy of PTSD in the U.S. Department of Veterans Affairs: Diagnostic- and Symptom-Guided Drug Selection," J. Clin. Psychiatry, 69: 959-965 (2008).
Mokni, et al., "Concerted Regulation of cGMP and cAMP Phoshpodiesterases in Early Cardiac Hypertrophy Induced by Angiotensin II," PLoS One, 5(12): e14227, 15 pages (2010).
Morgan, C., et al., "Acoustic Startle in Individuals With Post-traumatic Stress Disorder," Psychiatric Annals, 28(8): 430-434 (1998).
Mulrooney, C.A., "Recent Developments in Copper-Catalyzed N-Arylation with Aryl Halides," Essay—University of Pennsylvania.
Murakami, et al., Chem. Pharm. Bull., 43(8): 1281-1286 (1995).
Murray, et al., "Expression and activity of cAMP phosphodiesterase isoforms in pulmonary artery smooth muscle cells from patients with pulmonary hypertension: role for PDE1," Am. J. Physiol., 292: L294-L303 (2007).
Murray, T., et al., "LY503430, A Novel α-Amino-3-hydroxy-5-methylisoxazole-4-propionic Acid rEceptor Potentiator with Functional, Neuroprotective and Neurotrophic Effects in Rodent Models of Parkinson's Disease," The Journal of Pharmacology and Experimental Therapeutics, 306(2): 752-762 (2003).
Nagai, Y., et al., "Synthesis of 2,3,4,4a,5,9b-Hexahydro-1H-pyrido[4,3-b]indole Derivatives and Their Central Nervous System Activities," Journal of Medicinal Chemistry, 22(6): 677-683 (1979).
Newman, A., et al., "Solid-state analysis of the active pharmaceutical ingredient in drug products," Drug Discovery Today, 8(9): 898-903 (2003).
Nihon rounen igaku zasshi, 48(3): 195-204 (2011) (English Translation Only, 2 Pages).

Nishi, A., et al., "Advanced Research on Dopamine Signaling to Develop Drugs for the Treatment of Mental Disorders: Biochemical and Behavioral Profiles of Phosphodiesterase Inhibition in Dopaminergic Neurotransmission," J. Pharmacol. Sci., 114: 6-16 (2010).
Noble, F., et al., "The opioid receptors as targets for drug abuse medication," British Journal of Pharmacology, 172: 3964-3979 (2015).
Noguchi, M., et al., "A Facile Preparation of 7-(Substituted Amino-)-6H-pyrrolo[3,4-d]-pyrimidine Derivatives," Bulletin of the Chemical Society of Japan, 62(9): 3043-3045 (1989).
"Novel PDE Inhibitors for Treatment of Cognitive Dysfunction in Schizophrenia," 3 pages, accessed Mar. 26, 2014, (2014), URL: <http://sbir.gov/sbirsearch/detail/201838>.
O'Carroll, R., "Cognitive Impairment in Schizophrenia," Advances in Psychiatric Treatment, 6: 161-168 (2000).
Pardo, C., et al., "Synthesis of 1-(p-Nitrobenzyl)Azoles and 1-(p-Nitrobenzyl)Benzazoles," OPPI Briefs, 32(4): 385-390 (2000).
Park, E., et al., "Traumatic Brain Injury: Can the Consequences be Stopped?" CMAJ, 178(9): 1163-1170 (2008).
Patani, G., et al., "Bioisosterism: A Rational Approach in Drug Design," Chemical Reviews, 96(8): 3147-3176 (1996).
PDE1—(http://en.wikipedia.org/wiki/PDE1), 6 pages, 2014.
Perlis, R.H., et al., "Clinical Features of Bipolar Depression Versus Major Depressive Disorder in Large Multicenter Trials," Am. J. Psychiatry, 163: 225-231 (2006).
Pieniaszek, H., et al., "Moricizine Bioavailability via Simultaneous, Dual, Stable Isotope Administration: Bioequivalence Implications," J. Clin. Pharmacol., 39: 817-825 (1999).
Pine, A., et al., "Dopamine, Time, and Impulsivity in Humans," The Journal of Neuroscience, 30(26): 8888-8896 (2010).
Polli, et al., "Expression of a Calmodulin-Dependent Phosphodiesterase Isoform (PDE1 B1) Correlates with Brain Regions Having Extensive Dopaminergic Innervation," The Journal of Neuroscience, 14: 1251-1261 (1994).
Porsolt, R., et al., "Depression: A New Animal Model Sensitive to Antidepressant Treatments," Nature, 266: 730-732 (1977).
Poulsen, S., et al., "High-Pressure Synthesis of Enantiomerically Pure C-6 Substituted Pyrazolo[3,4-d]pyrimidines," Bioorganic & Medicinal Chemistry Letters, 11: 191-193 (2001).
Press Release, "Intra-Cellular Therapies Announces Additional Results From Phase I/II Clinical Trial for ITI-007 in Healthy Geriatric Subjects and Patients With Dementia," Intra-Cellular Therapies, Press Release Date: Nov. 21, URL: <http://ir.intracellulartherapies.com/releasedetail.cfm?ReleaseID=884325>.
Prickaerts, J., et al., "Possible Role of Nitric Oxide-Cyclic GMP Pathway in Object Recognition Memory: Effects of 7-Nitroindazole and Zaprinast," European Journal of Pharmacology, 337: 125-136 (1997).
"Protection for the Amino Group," Protective Groups in Organic Synthesis, Third Edition, John Wiley & Sons, Inc., 494-505 (1999).
Rackova, L., et al., "Free Radical Scavenging and Antioxidant Activities of Substituted Hexahydropyridoindoles. Quantitative Structure—Activity Relationships," J. Med. Chem., 49: 2543-2548 (2006).
Rainer, M.K., "Risperidone long-acting injection: a review of its long term safety and efficacy," Neuropsychiatric Disease and Treatment, 4(5): 919-927 (2008).
Ramaswamy, S., et al., "Failed efficacy of ziprasidone in the treatment of post-traumatic stress disorder," Contemporary Clinical Trials Communications, 2: 1-5 (2016).
Reed, et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 22(12): 5188-5197 (2002).
Rybalkin, et al., "Cyclic GMP Phosphodiesterases and Regulation of Smooth Muscle Function," Circ. Res., 93: 280-291 (2003).
Rybalkin, et al., "Cyclic Nucleotide Phosphodiesterase 1C Promotes Human Arterial Smooth Muscle Cell Proliferation," Circulation Research, 90(2): 151-157 (2002).
Rye, D.B., et al., "Sleep Disorders and Parkinson's Disease," American Parkinson Disease Association, Accessed Online, 2000, 2 pages, URL: <http://www.waparkinsons.org/edu_research/articles/Sleep_Disorders.html>.

(56) References Cited

OTHER PUBLICATIONS

Sadighi, J., et al., "A Highly Active Palladium Catalyst System for the Arylation of Anilines," Tetrahedron Letters, 39: 5327-5330 (1998).
Savjani, K., et al., "Drug Solubility: Importance and Enhancement Techniques," International Scholarly Research Newtwork Pharmaceutics, 2012: 1-10 (2012).
Schermuly, et al., "Phosphodiesterase 1 Upregulation in Pulmonary Arterial Hypertension," Circulation, 115: 2331-2339 (2007).
Schmidt, "Phosphodiesterase inhibitors as potential cognition enhancing agents," Current Topics in Medicinal Chemistry, 10(2): 222-230 (2010).
"Securities," Bennett v. Alkermes, Inc., 2003, URL: <http://securities.stanford.edu/filings-documents/1029/ALKS03-01/20031029_r01c_0312091.pdf>.
Semla, T., et al., "Off-Label Prescribing of Second-Generation Antipsychotics to Elderly Veterans with Posttraumatic Stress Disorder and Dementia," J. Am. Geriatr. Soc., 65: 1789-1795 (2017).
Sharma, et al., "Regulation of Calmodulin-Stimulated Cyclic Nucleotide Phoshpodiesterase (PDE1): Review," International Journal of Molecular Medicine, 18: 95-105 (2006).
Shimizu, et al., "Calmodulin-Dependent Cyclic Nucleotide Phosphodiesterase (PDE1) is a Pharmacological Target of Differentiation-Inducing Factor-1, an Antitumor Agent Isolated from Dictyostelium," Cancer Research, 64: 2568-2571 (2004).
Shook, et al., "Design and Characterization of Optimized Adenoside A2A/A1 Receptor Agonists for the Treatment of Parkinson's Disease," J. Med. Chem., 1-47 (2012).
Sigel, H., et al., "Ternary Complexes in Solution. XVI. Influence of the Size of the Chelate Rings on the Stability of Mixed-Ligand Copper(II) Complexes Containing Aliphatic Ligands," Inorganic Chemistry, 13(2): 462-465 (1974).
Silva, "Advances in Prodrug Design," Mini-Reviews in Medicinal Chemistry, 5: 893-914 (2005).
Singhal, D., et al., "Drug polymorphism and dosage form design: a practical perspective," Advanced Drug Delivery Reviews, 56: 335-347 (2004).
Skoog, "Principles of Instrumental Analysis, 4th Edition," 577 (1992).
Smith, et al., "Oxford Dictionary of Biochemistry and Molecular Biology," Oxford University Press, 145 (1997).
Snyder, G., et al., "Functional profile of a novel modulator of serotonin, dopamine, and glutamate neurotransmission," Psychopharmacology, 232: 605-621 (2015).
Snyder, G., et al., "Intracellular Signaling and Approaches to the Treatment of Schizophrenia and Associated Cognitive Impairment," Current Pharmaceutical Design, 20(31): 5093-5103 (2014).
Snyder, G., et al., "Preclinical Profile of ITI-214, an inhibitor of Phosphodiesterase 1, for Enhancement of Memory Performance in Rats," Psychopharmacology, 233: 3113-3124 (2016).
Southwick, S., "Neuroendocrine Alterations in Posttraumatic Stress Disorder," Psychiatric Annals, 28(8): 436-442 (1998).
Sugahara, M., et al., "A Facile Copper-Catalyzed Ullmann Condensation: N-Arylation of Heterocyclic Compounds Containing an -NHCO-Moiety," Chem. Pharm. Bull., 45(4): 719-721 (1997).
Suiciak, J.A., "The Role of Phosphodiesterases in Schizophrenia: Therapeutic Implications," CNS Drugs, 22(12): 983-993 (2008).
Takahashi, et al., "Measurement of Intracellular Calcium," Physiological Reviews, 79(4): 1089-1125 (1999).
Takimoto, E., "Controlling Myocyte cGMP, Phosphodiesterase 1 Joins the Fray," Circulation Research, 105: 931-933 (2009).
Taragano, F., et al., "A Double-Blind, Randomized, Fixed-Dose Trial of Fluoxetine vs. Amitriptyline in the Treatment of Major Depression Complication Alzheimer's Disease," Psychosomatics, 38(8): 246-252 (1997).
Tariot, P., et al., "Memantine Treatment in Patients With Moderate to Severe Alzheimer Disease Already Receiving Donepezil," JAMA, 291(3): 317-324 (2004).
Tonn, G.R., et al., "Simultaneous Analysis of Diphenhydramine and a Stable Isotope Analog (2H10)diphenhydramine Using Capillary Gas Chromatography with Mass Selective Detection in Biological Fluids from Chronically Instrumented Pregnant Ewes," Biol. Mass. Spectrom., 22(11): 633-642 (1993).
Turko, I., et al., "Inhibition of Cyclic GMP-Binding Cyclic GMP-Specific Phosphodiesterase (Type 5) by Sildenafil and Related Compounds," Molecular Pharmacology, 56: 124-130 (1999).
Ungerstedt, U., et al., "Quantitative Recording of Rotational Behavior in Rats After 6-Hydroxy-dopamine Lesions of the Nigrostriatal Dopamine System," Brain Research, 24: 485-493 (1970).
Ungerstedt, U., et al., "Stereotaxic Mapping of the Monoamine Pathways in the Rat Brain," Acta Physiologica Scandinavica, Supplementum 367: 1-48 (1971).
Upfal, J., "The Australian Drug Guide," Seventh Edition, Black Ink, Melbourne, Australia, 321-324 (2007).
Vas, A., et al., "Clinical and non-clinical investigations using positron emission tomography, near infrared spectroscopy and transcranial Doppler methods on the neuroprotective drug vinpocetine: A summary of evidences," Journal of the Neurological Sciences, 259-262 (2002).
Vatter, et al., "Differential Phosphodiesterase Expression and Cytosolic Ca2+ in Human CNS Tumour Cells and in Non-Malignant and Malignant Cells of Rat Origin," J. of Neurochemistry, 93: 321-329 (2005).
Wagaw, S., et al., "A Palladium-Catalyzed Method for the Preparation of Indoles via the Fischer Indole Synthesis," Journal of the American Chemical Society, 121(44): 10251-10263 (1999).
Wallis, et al., "Tissue distribution of phosphodiesterase families and the effects of sildenafil on tissue cyclic nucleotides, platelet function, and the contractile responses of trabeculae carneae and aortic rings in vitro," Am. J. Cardiol., 83(5A): 3C-12C (1999).
Wermuth, CG., ed., "Molecular Variations based on isoteric replacements," The Practice of Chemistry, Technomics, Inc., 1(13): 235-271 (1998) (Japanese translated version).
Weschules, D., et al., "Acetylcholinesterase Inhibitor and N-Methyl-D-Aspartic Acid Receptor Antagonist Use among Hospice Enrollees with a Primary Diagnosis of Dementia," Journal of Palliative Medicine, 11(5): 738-745 (2008).
Wiese, M., "DSC Detection of Polymorphism in Pharmaceutical Anhydrous Dexamethasone Acetate," TA Instruments, TA302, 1-4 (2002).
Willerson, et al., "Inflammation as a Cardiovascular Risk Factor," Circulation, 109: II-2-II-10 (2004).
Wolen, R.L., "The Application of Stable Isotopes to Studies of Drug Bioavailability and Bioequivalence," J. Clin. Pharmacol., 26(6): 419-424 (1986).
Wolfe, J., et al., "An Improved Catalyst System for Aromatic Carbon-Nitrogen Bond Formation: The Possible Involvement of Bis(Phosphine) Palladium Complexes as Key Intermediates," J. Am. Chem. Soc., 118: 7215-7216 (1996).
Wolfe, J., et al., "Intramolecular Palladium-Catalyzed Aryl Amination and Aryl Amidation," Tetrahedron, 52(21): 7525-7546 (1996).
Wolff, Manfred E., Burger's Medicinal Chemistry and Drug Discovery, Fifth Ed., vol. 1: Principles and Practice, John Wiley & Sons, 975 (1995).
Wolter, M., et al., "Synthesis of N-Aryl Hydrazides by Copper-Catalyzed Coupling of Hydrazides with Aryl Iodides," Organic Letters, 3(23): 3803-3805 (2001).
Written Opinion of the International Searching Authority for International Application No. PCT/US2014/025666, dated Jul. 7, 2015, 4 pages.
Xia, et al., "Synthesis and Evaluation of Polycyclic Pyrazolo[3,4-d]pyrimidines as PDE1 and PDE5 cGMP Phosphodiesterase Inhibitors," J. Med. Chem., 40: 4372-4377 (1997).
Yamada, K., et al., "A Mild Copper-mediated Intramolecular Amination of Aryl Halides," Synlett, 2: 231-234 (2002).
Yang, B., et al., "The development of efficient protocols for the palladium-catalyzed cyclization reactions of secondary amides and carbamates," Organic Letters, 1(1): 35-37 (1999).
Youdim, MB., "The Path from Anti Parkinson Drug Selegiline and Rasagiline to Multifunctional Neuroprotective Anti Alzheimer Drugs Ladostigil and M30," Curr. Alzheimer, Res., 3(5): 541-550 (2006).

(56) References Cited

OTHER PUBLICATIONS

Yudofsky, S., et al., "Propanolol in the Treatment of Rage and Violent Behavior in Patients with Chronic Brain Syndromes," Am. J. Psychiatry, 138(2): 218-220 (1981).

Zhang, et al., "Phosphodiesterases and cardiac cGMP: evolving roles and controversies," Trends in Pharmacological Sciences, 32(6): 360-365 (2011).

Zhang, G., et al., "The role of serotonin 5-HT2A receptors in memory and cognition," Frontiers in Pharmacology, 6(225): 1-17 (2015).

Zhang, Z., et al., "Highly efficient copper-catalyzed N-arylation of alkylamines with aryl iodides using phosphoramidite as ligand," Catalysis Communications, 6: 784-787 (2005).

COMPOSITIONS AND METHODS

CROSS-REFERENCE TO RELATED APPLICATIONS

This application is a United States Application under 35 U.S.C. § 371 claiming priority to and the benefit of PCT Application No. PCT/US2017/024575, filed Mar. 28, 2017, which claims priority to and the benefit of U.S. Provisional Application No. 62/314,314, filed Mar. 28, 2016, the contents of each of which are hereby incorporated by reference in their entireties.

TECHNICAL FIELD

The present invention relates to use of (i) a 5-HT2A or 5-HT2A/D2 receptor ligand, for example a substituted heterocycle fused gamma-carbolines as described herein, in free, pharmaceutically acceptable salt or prodrug form, and (ii) a cyclic nucleotide phosphodiesterase 1 (PDE1) inhibitor, for example a 7,8-dihydro-imidazo[1,2-a]pyrazolo[4,3-e]pyrimidin-4-one compounds, in combination (sequentially or simultaneously, or in the form of a fixed dose combination for the prophylaxis or treatment of one or more disorders associated with dementia (including behavioral or mood disturbances (e.g., agitation/aggression), psychosis, depression and/or sleep disturbances), or enhancing cognition, for example in schizophrenia or dementia.

BACKGROUND OF THE INVENTION

Dementia is a disorder characterized by the loss of cognitive abilities affecting memory, reasoning, judgment and behavior. At an early stage of dementia, people may experience mild cognitive impairment (MCI, also known as incipient dementia, or isolated memory impairment) which is cognitive impairment beyond that expected based on the age and education of the individual, but which is not significant enough to interfere with their daily activities. Studies suggest that these individuals tend to progress to probable Alzheimer's disease at a rate of approximately 10% to 15% per year. Alzheimer's disease is the most common type of dementia and is an irreversible, progressive neurodegenerative disease that disrupts memory, perception, reasoning, judgment, information processing, emotional behavior, personality as well as social and occupational functions. Of date, 5.4 million of Americans are believed to be living with Alzheimer's and nearly 36 million people worldwide are believed to be living with this disease or other dementias.

Currently, there is no cure or standard of treatment for dementia. Available treatments are palliative and symptomatic in nature aiming to manage and slow the progression of the cognitive manifestation of the disease. Drugs approved in the United States for the treatment of Alzheimer's disease, which are also used to treat dementia in general include acetylcholinesterase inhibitors (e.g., Tacrine, rivastigmine (Exelon), donepezil (Aricept), and galantamine (Razadyne, formerly called Reminyl)) and NMDA receptor antagonist (e.g., memantine (Namenda)). While these drugs improve mental function (such as memory, attention, social interaction, reasoning ability, language ability, and ability to perform activities of daily living), they often cause side effects including stomach upset, diarrhea, nausea, vomiting, muscle cramps, fatigue, difficulty falling or staying asleep or excess sleepiness, depression, bradycardia and other side effects. In addition, these drugs do not treat affective symptoms and/or other behavior disruptions such as mood swing, agitation, aggressive/assaultive behavior and paranoia which are common in dementias. In fact, some studies have shown that memantine, a drug approved for Alzheimer's disease and often used for dementias in general, may have some adverse effects on neuropsychiatric functioning, particularly agitation/aggression, delusions or hallucinations. These untreated and sometimes aggravated behavioral disruptions often prevent the patients from integrating back into society, causing further distress to the caregivers and eventually leading to the patients' institutionalization. To control aggression and psychosis in dementia, particularly in Alzheimer's disease, antipsychotic drugs are used. However, antipsychotic drugs such as haloperidol, risperidone and quetiapine are associated with serious side effects including extrapyramidal side effects (akinesia or akathisia), bone marrow suppression, seizure, orthostatic hypotension, insomnia, sedation, somnolence and weight gain. Many atypical antipsychotic agents also have a higher risk of heart failure. Therefore, the use of these antipsychotic agents in combination with anticholinesterase inhibitor or NMDA receptor antagonist is undesirable.

In addition to behavior and mood disturbances, many dementia patients, particularly those at a more serious stage of the disease also commonly experience sleep disturbances wherein the patients either have difficulty falling asleep, maintaining sleep or experience changes in their sleep-wake cycle/pattern. These patients may also feel restless or agitated in the late afternoon or early evening (often called "sundowning"). In fact, studies have shown evidence that a loss in the suprachiasmatic nucleus (SCN) neuronal population coincides with Alzheimer's patients' stage of dementia. This loss of SCN neuronal population appears to be causative in the observed disturbances in melantonin rhythm which may underlie accompanying sleep disturbances. While agents such as temazepam (Restoril), zolpidem (Ambien), or zaleplon (Sonata), or sedating antidepressants, such as trazodone (Desyrel, Molipaxin), may be useful in managing insomnia, failure of these drugs to improve sleep quality in addition to the associated risk of falling due to drowsiness and psychomotor impairment caused by these agents render them undesirable for dementia, particularly Alzheimer's patients.

Particularly in later stages of dementia, patients may suffer psychosis. While psychosis is often associated with schizophrenia in young people, people with dementia may, as the disease progresses, exhibit a spectrum of behaviors from agitation to positive symptoms of psychosis such as paranoia, delusions and hallucinations. The patients may also suffer negative symptoms such as emotional withdrawal, passive social withdrawal, and stereotyped thinking, and symptoms of general psychopathology including active social avoidance, anxiety, tension, and somatic concerns. These negative symptoms are often accompanied by depression, cognitive dysfunction and insomnia. Collectively, these residual phase symptoms are not well-treated by many antipsychotic drugs currently available on the market and therefore are usually most apparent when the more dramatic positive or active phase symptoms have been brought under control by antipsychotic medications.

There remains an urgent need for an effective therapeutic regime for the prophylaxis or treatment of dementia and disorders associated thereof, particularly to alleviate behavioral/mood disturbances (e.g., agitation, aggressive/assaultive behavior) and sleep disturbances in patients suffering from dementia or psychosis associated with dementia.

Substituted heterocycle fused gamma-carbolines are known to be 5-HT2A or 5-HT2A/D2 receptor ligands, useful in treating central nervous system disorders. These compounds have been disclosed in U.S. Pat. Nos. 6,548,493; 7,238,690; 6,552,017; 6,713,471; U.S. RE39680, and U.S. RE39679, as novel compounds useful for the treatment of disorders associated with 5-HT2A receptor modulation such as obesity, anxiety, depression, psychosis, schizophrenia, sleep disorders, sexual disorders, migraine, conditions associated with cephalic pain, and social phobias. PCT/US08/03340 and U.S. Pat. No. 7,081,455 also disclose methods of making substituted heterocycle fused gamma-carbolines and uses of these gamma-carbolines as serotonin agonists and antagonists useful for the control and prevention of central nervous system disorders such as addictive behavior and sleep disorders. WO 2009/145900 and WO 2013/155506, each incorporated herein by reference, disclose use of specific substituted heterocycle fused gamma-carbolines for the treatment of a combination of psychosis and depressive disorders as well as sleep, depressive and/or mood disorders in patients with psychosis or Parkinson's disease and for the treatment or prophylaxis of disorders associated with dementia, particularly behavioral or mood disturbances such as agitation, irritation, aggressive/assaultive behavior, anger, physical or emotional outbursts and psychosis and sleep disorders associated with dementia.

PDE1 is a $Ca^{2+}$-calmodulin-dependent phosphodiesterase (CaM-PDE), which can downregulate intracellular cAMP and cGMP signaling by hydrolyzing these cyclic nucleotides to their respective inactive 5'-monophosphates (5'AMP and 5'GMP). PDE1 plays a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of PDE1, resulting in reduced cAMP and cGMP. Dopamine D1 receptor activation, on the other hand, leads to activation of calcium dependent nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Inhibition of PDE1 can thus potentiate the effect of a dopamine D1 agonist by protecting cGMP and cAMP from degradation, and likewise can inhibit dopamine D2 receptor signaling pathways, by inhibiting PDE1 activity. WO 2014/145617, incorporated herein by reference, e.g., for its disclosure of PDE1 inhibitors, describes the use of PDE1 inhibitors as neuroprotective agents and/or neural regenerative agents, e.g. to prevent the development of a CNS disease or disorder in an individual at risk for the development of a CNS disease or disorder. By facilitating increased levels of intracellular cAMP and/or cGMP, PDE1 inhibitors can initiate the transcription of genes that are necessary for overcoming myelin inhibition of regeneration after nerve injury and promoting neurite outgrowth and/or axonal regeneration in the case of a CNS disease, disorder, or injury, thus encouraging axonal regeneration and/or neuroprotection while simultaneously decreasing or lessening damage associated with chronically elevated intracellular calcium levels, which can lead to calmodulin activation of PDE1.

New methods of treating and improving the quality of life in patients having dementia and slowing the progression of dementia are urgently needed.

SUMMARY OF THE INVENTION

The invention provides a method of treating dementia (including associated disorders such as behavioral or mood disturbances (e.g., agitation/aggression), psychosis, depression and/or sleep disturbances), and/or enhancing cognition, for example in patients suffering from schizophrenia or dementia, comprising administering an effective amount of (i) a 5-HT2A or 5-HT2A/D2 receptor ligand, for example a substituted heterocycle fused gamma-carbolines as described herein, in free, pharmaceutically acceptable salt or prodrug form, together with (ii) a PDE1 inhibitor, as described herein. The 5-HT2A/D2 ligand promotes quality of sleep and reduces agitation, while the PDE1 inhibitor promotes cognitive function. The administration may be sequential or simultaneous. The invention further provides a pharmaceutical composition, e.g., for use in such a method, comprising (i) a 5-HT2A or 5-HT2A/D2 receptor ligand and (ii) a PDE1 inhibitor.

DETAILED DESCRIPTION

Administration of a PDE1 inhibitor as described herein will enhance cognition and also act to increase levels of intracellular cAMP and initiate the transcription of genes that are necessary for overcoming the inhibition of axonal regeneration and promoting neurite outgrowth and/or axonal regeneration thus inhibiting the neurodegenerative process. For instance, increased intracellular cAMP, such as would result from PDE1 inhibition, leads to increased activity of cAMP-dependent proteins, such as protein kinase C (PKC).

Another benefit of the administration of a PDE1 inhibitor of the invention is an increase in intracellular cGMP. This increase in intracellular cGMP may lead to an increase in the activity of PKG, preventing a further rise in intracellular calcium levels. Thus, it is believed that the administration of a PDE1 inhibitor could have the dual benefit of, for example, playing a beneficial role in axonal regeneration (and/or neuroprotection) while simultaneously decreasing the deleterious effects that may be associated with elevated intracellular calcium levels.

The 5-HT2A or 5-HT2A/D2 receptor ligand is a compound which antagonizes serotonin-2A (5-HT2A) receptor, and/or modulates dopamine receptor signaling at the level of key intra-cellular phosphoproteins and therefore is useful for the treatment of not only acute symptoms, but also residual symptoms of pyschosis, particularly schizophrenia. At dopamine D2 receptors, these compounds have dual properties and act as both post-synaptic antagonists and pre-synaptic partial agonists. They also stimulate phosphorylation of glutamatergic NMDA NR2B, or GluN2B, receptors in a mesolimbic specific manner. It is believed that this regional selectivity in the brain areas thought to mediate the efficacy of antipsychotic drugs, together with serotonergic, glutamatergic, and dopaminergic interactions, may result in antipsychotic efficacy for positive, negative, affective and cognitive symptoms associated with schizophrenia. The compounds also exhibit serotonin reuptake inhibition, providing antidepressant activity for the treatment of schizoaffective disorder, co-morbid depression, and/or as a stand-alone treatment for major depressive disorder. The 5-HT2A or 5-HT2A/D2 receptor ligands as described are also useful for the treatment of bipolar disorder and other psychiatric and neurodegenerative disorders, particularly behavioral disturbances associated with dementia, autism and other CNS diseases. These features may be able to improve the quality of life of patients with schizophrenia and enhance social function to allow them to more fully integrate into their families and their workplace. At a low-dose, the Thus, the combination of the PDE1 inhibitor with a 5-HT2A or 5-HT2A/D2 receptor ligand will be particularly useful, e.g., in the treatment of dementia or psychosis (e.g., schizophrenia) and disorders associated thereof. At lower doses, they are useful in treating sleep, aggression and agitation. At a high-dose, they can treat acute exacerbated and residual schizophrenia, bipolar disorders, and mood disorders.

As 5-HT2A or 5-HT2A/D2 receptor ligand compounds used in the current disclosure are effective in treating not just acute symptoms, but also residual symptoms of psychosis, their combination with a PDE1 inhibitor disclosed herein, which is believed to provide a neuroprotective effect, is useful in the treatment of a wide range of symptoms and disorders associated with dementia or psychosis such as schizophrenia.

Therefore, in a particular embodiment, the invention provides a method (Method I) for the prophylaxis or treatment of one or more disorders associated with dementia (e.g., disorders associated with mild to severe cognition impairment and dementing illnesses including senile dementia, Alzheimer's disease, Pick's disease, frontotemporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease; and further including behavioral or mood disturbances (e.g., agitation/aggression), psychosis, depression and/or sleep disturbances, as well as enhancing cognition, for example in schizophrenia or dementia) comprising administering to a patient in need thereof, a therapeutically effective amount of
(i) a 5-HT2A or 5-HT2A/D2 receptor ligand, for example a compound of Formula I:

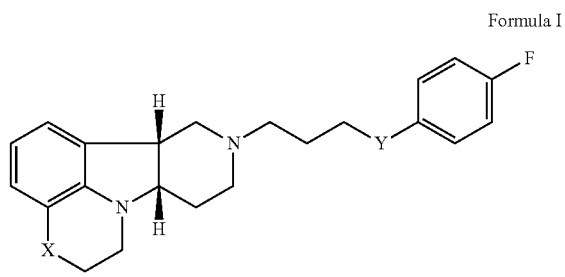

Formula I wherein:
X is —N(H)—, —N($CH_3$)— or —O—;
Y is —C(═O)—, —C(H)(OH)— or —C(H)($OR_1$)—;
$R_1$ is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, —C(O)—$C_9$alkyl, —C(O)—$C_{11}$alkyl, —C(O)—$C_{13}$alkyl or —C(O)—$C_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand),
in free, pharmaceutically acceptable salt or prodrug form;

and
(ii) a PDE1 inhibitor, for example a compound according to Formula II

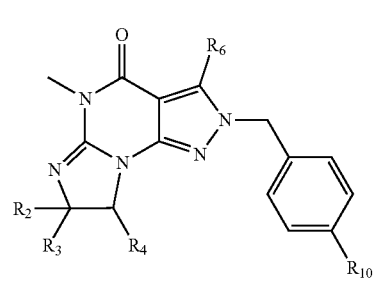

Formula II wherein
$R_2$ is H and $R_3$ and $R_4$ together form a tri- or tetramethylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];
$R_6$ is (optionally halo-substituted) phenylamino or (optionally halo-substituted) benzylamino;
$R_{10}$ is (optionally halo-substituted) phenyl, (optionally halo-substituted) pyridyl (for example 3-fluoropyrid-2-yl), or thiadiazolyl (e.g., 1,2,3-thiadiazol-4-yl); in free or pharmaceutically acceptable salt form.

For example, Method 1 may be as follows:
1.1. Method I, wherein X in the compound of Formula I is —N(H)—, —N($CH_3$)— or —O—;
1.2. Method I or 1.1, wherein X in the compound of Formula I is —N(H);
1.3. Method I or 1.1, wherein X in the compound of Formula I is —N($CH_3$)—;
1.4. Method I or 1.1, wherein X in the compound of Formula I is —O—;
1.5. Method I or any of formulae 1.1-1.4, wherein Y in the compound of Formula I is —C(═O)—, —C(H)(OH)— or —C(H)($OR_1$)—;
1.6. Method I or any of formulae 1.1-1.4, wherein Y in the compound of Formula I is —C(═O)—;
1.7. Method I or any of formulae 1.1-1.4, wherein Y in the compound of Formula I is —C(H)(OH)—;
1.8. Method I or any of formulae 1.1-1.4, wherein Y in the compound of Formula I is —C(H)($OR_1$)—;
1.9. Method I or 1.8, wherein $R_1$ in the compound of Formula I is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, —C(O)—$C_9$alkyl, —C(O)—$C_{11}$alkyl, —C(O)—$C_{13}$alkyl or —C(O)—$C_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand); e.g., wherein $R_1$ in the compound of Formula I is —C(O)—$C_{6-15}$alkyl, e.g., —C(O)—$C_9$alkyl; or wherein $R_1$ in the compound of Formula I is —C(O)—$C_{1-5}$alkyl, e.g., —C(O)—$C_3$alkyl.

1.10. Method I or any of 1.1-1.5 or 1.7, wherein the Compound of Formula I is:

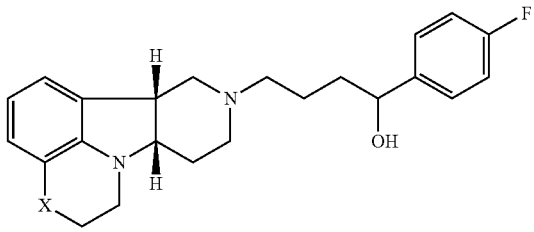

1.11. Method I or any of 1.1-1.5 or 1.7, wherein the Compound of Formula I is:

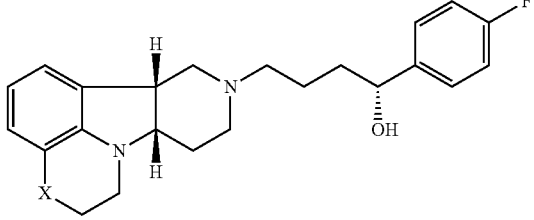

1.12. Any foregoing Method 1, or 1.1-1.3, 1.5, or 1.9 wherein the Compound of Formula I is

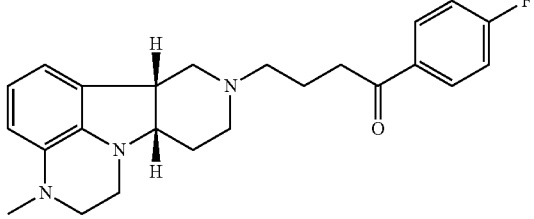

1.13. Method 1.12 wherein the Compound of Formula 1 is in the form of the tosylate salt.
1.14. Method 1.12 wherein the Compound of Formula 1 is in the form of the free base.
1.15. Any foregoing Method wherein, in the Compound of Formula II, $R_6$ is phenylamino or 4-fluorophenylamino.
1.16. Any foregoing Method wherein, in the Compound of Formula II, $R_{10}$ is 3-fluoropyrid-2-yl or methylcarbonyl.
1.17. Any foregoing Method wherein, in the Compound of Formula II, $R_6$ is phenylamino or 4-fluorophenylamino and $R_{10}$ is 3-fluoropyrid-2-yl or methylcarbonyl.
1.18. Any foregoing Method wherein the Compound of Formula II is

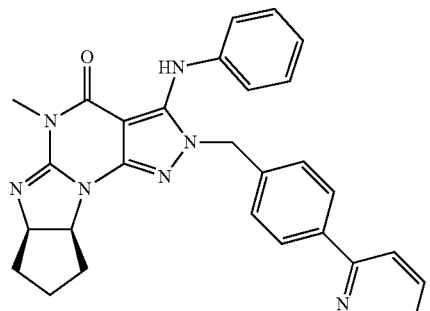

or

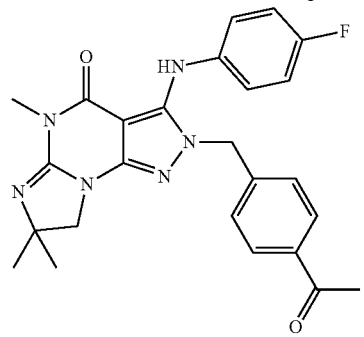

in free or pharmaceutically acceptable salt form.
1.19. Method 1.16 wherein the Compound of Formula II is in the form of the monophosphate salt.
1.20. Any foregoing Method, wherein the Compound of Formula I is:

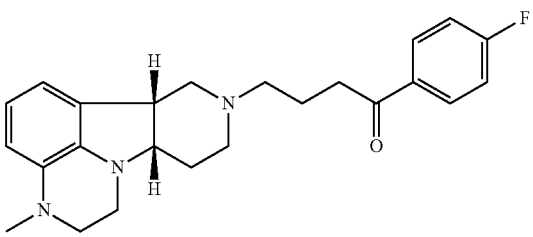 [SMILES: CN1CCN2c3c(cccc31)[C@@H]1CN(CCCC(=O)c3ccc(F)cc3)CC[C@@H]12]

in free of pharmaceutically acceptable salt form, e.g., tosylate salt form; and the Compound of Formula II is:

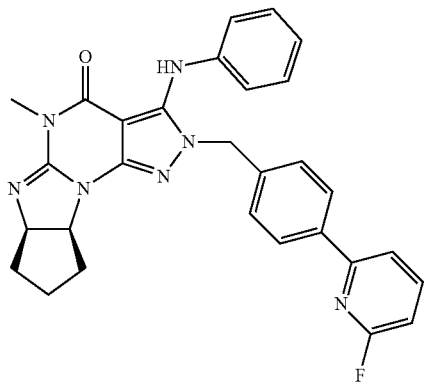 [SMILES: CN1C(=O)c2c(nn(Cc3ccc(-c4cccc(F)n4)cc3)c2Nc2ccccc2)N2C1=N[C@@H]1CCC[C@@H]12]

in free of pharmaceutically acceptable salt form, e.g., monophosphate salt form.

1.21. Any foregoing Method comprising administration of a pharmaceutical composition comprising effective amounts of both a Compound of Formula I and a Compound of Formula II.

1.22. Any foregoing method wherein the daily dosage of the Compound of Formula 1 is 1 mg to 10 mg.

1.23. Any foregoing method wherein the daily dosage of the Compound of Formula 1I is 0.1 mg to 10 mg.

1.24. Any foregoing method wherein the Compound of Formula I is:

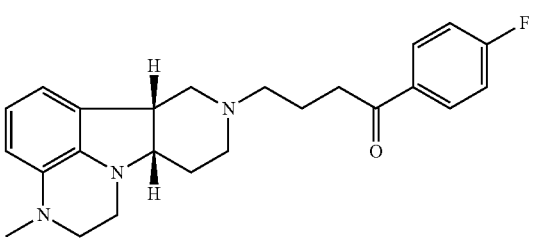 [SMILES: CN1CCN2c3c(cccc31)[C@@H]1CN(CCCC(=O)c3ccc(F)cc3)CC[C@@H]12]

in free or pharmaceutically acceptable salt form, administered in a daily dose of 1 mg to 10 mg, e.g., 2 mg to 7 mg, the dosage calculated as the free base equivalent; and the Compound of Formula II is:

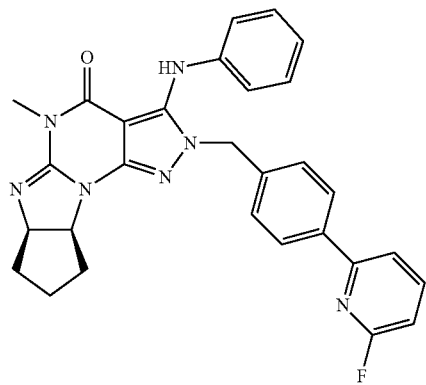 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form, administered in a daily dose of 0.5 mg to 10 mg, e.g. 0.5 to 2 mg, or 1 to 5 mg, the dosage calculated as the free base equivalent.

1.25. Method 1.21 wherein the compound of Formula 1 is in tosylate salt form administered in a daily dose equivalent to 1 to 5 mg of free base, the compound of Formula II is in monophosphate salt form administered in a daily dose equivalent to 0.5 to 2 mg of free base.

1.26. Any foregoing Method wherein the compound of Formula I and/or of Formula II is deuterated, e.g., wherein the deuterium:protium ratio at a specified position in the molecule is significantly higher, e.g., at least 2×, for example at least 10× higher, than the natural isotope ratios.

1.27. Any foregoing Method wherein the Compound of Formula I is a Compound of Formula 1 as described in WO 2015/154025, the contents of which are incorporated herein by reference, e.g., wherein the —CH2- adjacent to X and/or Y is —CHD- or —CD2-.

1.28. Method 1.22 wherein the method comprises once daily administration of a unit dosage for oral administration, for example a tablet or capsule, comprising the compound of Formula I in tosylate salt form in an amount equivalent to 1 to 5 mg of free base, the compound of Formula II in monophosphate salt form in an amount equivalent to 0.5 to 2 mg of free base, and a pharmaceutically acceptable diluent or carrier.

1.29. Any foregoing method wherein the disorders associated with dementia are disorders associated with Huntington's disease, Parkinson's disease, Mulitple sclerosis, Amyotrophic lateral sclerosis, Down syndrome, Eldery depression, Wernicke-Korsakoff's syndrome, corticobasal degenerations, and prion disease.

1.30. Any foregoing method wherein the disorders associated with dementia are disorders associated with mild cognition impairment and dementing illnesses including senile dementia, Alzheimer's disease, Pick's disease, frontotemporal dementia, parasupranuclear palsy, dementia with Lewy bodies and vascular dementia.

1.31. Any foregoing method wherein the disorders associated with dementia are disorders associated with senile dementia, Alzheimer's disease, Pick's disease, frontotemporal dementia, parasupranuclear palsy, dementia with Lewy bodies and vascular dementia.

1.32. Any foregoing method wherein the disorders associated with dementia are disorders associated with Alzheimer's disease.

1.33. Any foregoing method wherein the disorders associated with dementia are disorders associated with mild cognition impairment.

1.34. Any foregoing method wherein the disorder associated with dementia to be treated is selected from the group consisting of (1) behavioral or mood disorders such as agitation/irritation, aggressive/assaultive behavior, anger, physical or emotional outbursts; (2) psychosis; (3) depression; and (4) sleep disorders in patients suffering from dementia, particularly Alzheimer's disease.

1.35. Any foregoing method wherein the disorder to be treated is psychosis in a patient with dementia, particularly Alzheimer's disease.

1.36. Any foregoing method wherein the disorder to be treated is depression in a patient with dementia, particularly Alzheimer's disease.

1.37. Any foregoing method wherein the disorder to be treated is behavioral or mood disorders such as agitation/irritation, aggressive/assaultive behavior, anger, physical or emotional outbursts in a patient with dementia, particularly Alzheimer's disease.

1.38. Any foregoing method wherein the disorder to be treated is sleep disorders in a patient with dementia, particularly Alzheimer's disease.

1.39. Any of Method I et seq. wherein the disorder to be treated is sleep maintenance insomnia, frequent awakenings, and waking up feeling unrefreshed in a patient with dementia, particularly Alzheimer's disease.

1.40. Any foregoing method wherein the disorder to be treated is sleep maintenance insomnia in a patient with dementia, particularly Alzheimer's disease.

1.41. Any of Method I et seq. wherein the disorder to be treated is advanced sleep-phase syndrome in a patient with dementia, particularly Alzheimer's disease.

1.42. Any foregoing method wherein the disorder to be treated is delayed sleep-phase syndrome in a patient with dementia, particularly Alzheimer's disease.

1.43. Any foregoing method wherein the disorder associated with dementia is selected from behavioral or mood disturbances (e.g., agitation/aggression), psychosis, depression and/or sleep disturbances.
1.44. Any foregoing method comprising enhancing cognition, for example in schizophrenia or dementia.
1.45. Any foregoing method further comprising administering one or more additional therapeutic agents useful for the prophylaxis or treatment of dementia, particularly Alzheimer's disease.
1.46. The foregoing method wherein the therapeutic agent useful for the prophylaxis or treatment of dementia, particularly Alzheimer's disease is a cholinesterase inhibitor (e.g., acetylcholinesterase inhibitor) or an N-Methyl D-Asparate (NMDA) receptor antagonist, in free or pharmaceutically acceptable salt form;
1.47. The foregoing method wherein the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form;
1.48. The foregoing method wherein the cholinesterase inhibitor (e.g., acetylcholinesterase inhibitor) is donepezil in free or pharmaceutically acceptable salt form;
1.49. Any foregoing method wherein the patient additionally receives a NMDA receptor antagonist, e.g., memantine in free or pharmaceutically acceptable salt form;
1.50. Any foregoing method further comprising administering one or more additional therapeutic agents useful for the prophylaxis or treatment of dementia, particularly Alzheimer's disease, wherein the therapeutic agent useful for the prophylaxis or treatment of dementia, particularly Alzheimer's disease is a combination of a cholinesterase inhibitor (e.g., acetylcholinesterase inhibitor) and an N-Methyl D-Asparate (NMDA) receptor antagonist, in free or pharmaceutically acceptable salt form.
1.51. The foregoing method wherein the one or more therapeutic agent(s) useful for the prophylaxis or treatment of dementia, particularly Alzheimer's disease or symptoms thereof is a combination of donepezil and memantine in free or pharmaceutically acceptable salt form.
1.52. Any foregoing method further comprising administering one or more therapeutic agents useful for the prophylaxis or treatment of dementia, particularly Alzheimer's disease further comprises administering one or more therapeutic agents selected from antidepressant compounds, compounds that modulate GABA activity (e.g., enhances the activity and facilitates GABA transmission), a GABA-B agonist, a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug, and an antipsychotic agent, e.g., an atypical antipsychotic agent, in free or pharmaceutically acceptable salt form.

In another aspect, the invention provides a pharmaceutical composition (Composition 1) [e.g., for the prophylaxis or treatment of one or more disorders associated with dementia (e.g., disorders associated with mild to severe cognition impairment and dementing illnesses including senile dementia, Alzheimer's disease, Pick's disease, frontotemporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease, e.g., for use in any of Methods 1 et seq.], comprising (i) a 5-HT2A or 5-HT2A/D2 receptor ligand, for example a compound of Formula I:

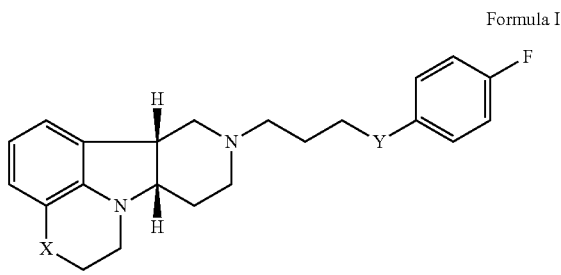

Formula I wherein:
X is —N(H)—, —N(CH₃)— or —O—;
Y is —C(=O), —C(H)(OH) or —C(H)(OR₁);
R₁ is —C(O)—C₁₋₂₁alkyl (e.g., —C(O)—C₁₋₅alkyl, —C(O)—C₆₋₁₅alkyl or —C(O)—C₁₆₋₂₁alkyl), preferably said alkyl is a straight chain, optionally saturated or unsaturated and optionally substituted with one or more hydroxy or C₁₋₂₂alkoxy (e.g., ethoxy) groups, for example R₁ is —C(O)—C₆alkyl, —C(O)—C₇alkyl, —C(O)—C₉alkyl, —C(O)—C₁₁alkyl, —C(O)—C₁₃alkyl or —C(O)—C₁₅alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand), in free, pharmaceutically acceptable salt or prodrug form; and (ii) a PDE1 inhibitor, for example a compound according to Formula II

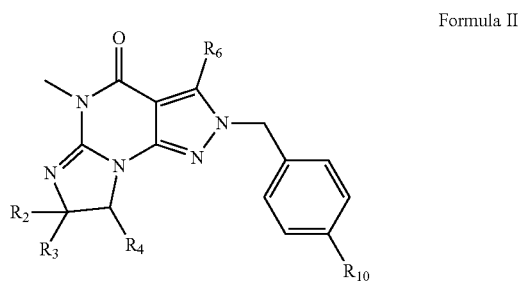

Formula II wherein
R₂ is H and R₃ and R₄ together form a tri- or tetramethylene bridge [pref. with the carbons carrying R₃ and R₄ having the R and S configuration respectively]; or R₂ and R₃ are each methyl and R₄ is H; or R₂ and R₄ are H and R₃ is isopropyl [pref. the carbon carrying R₃ having the R configuration];
R₆ is (optionally halo-substituted) phenylamino or (optionally halo-substituted) benzylamino; for example, phenylamino or 4-fluorophenylamino;

$R_{10}$ is methylcarbonyl, (optionally halo-substituted) phenyl, (optionally halo-substituted) pyridyl (for example 3-fluoropyrid-2-yl), or thiadiazolyl (e.g., 1,2,3-thiadiazol-4-yl);

in free or pharmaceutically acceptable salt form.

For example, Composition 1 includes, inter alia, the following embodiments:

1.1. Composition I, wherein X in the compound of Formula I is —N(H)—, —N(CH$_3$)— or —O—;

1.2. Composition I or 1.1, wherein X in the compound of Formula I is —N(H);

1.3. Composition I or 1.1, wherein X in the compound of Formula I is —N(CH$_3$)—;

1.4. Composition I or 1.1, wherein X in the compound of Formula I is —O—;

1.5. Composition I or any of formulae 1.1-1.4, wherein Y in the compound of Formula I is —C(═O), —C(H)(OH) or —C(H)(OR$_1$);

1.6. Composition I or any of formulae 1.1-1.4, wherein Y in the compound of Formula I is —C(═O);

1.7. Composition I or any of formulae 1.1-1.4, wherein Y in the compound of Formula I is —C(H)(OH);

1.8. Composition I or any of formulae 1.1-1.4, wherein Y in the compound of Formula I is —C(H)(OR$_1$);

1.9. Composition I or 1.8, wherein $R_1$ in the compound of Formula I is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example $R_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand); e.g., wherein $R_1$ in the compound of Formula I is —C(O)—C$_{6-15}$alkyl, e.g., —C(O)—C$_9$alkyl; or wherein $R_1$ in the compound of Formula I is —C(O)—C$_{1-5}$alkyl, e.g., —C(O)—C$_3$alkyl.

1.10. Composition I or any of 1.1-1.5 or 1.7, wherein the Compound of Formula I is:

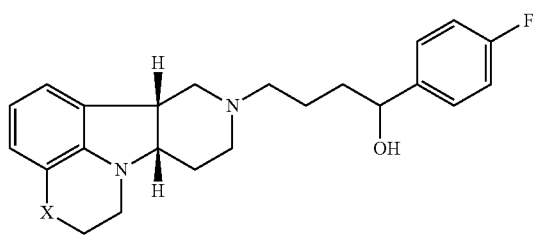

1.11. Composition I or any of 1.1-1.5 or 1.7, wherein the Compound of Formula I is:

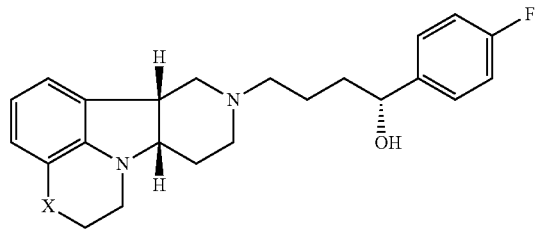

1.12. Composition I or any of 1.1-1.5 or 1.7, wherein the Compound of Formula I is:

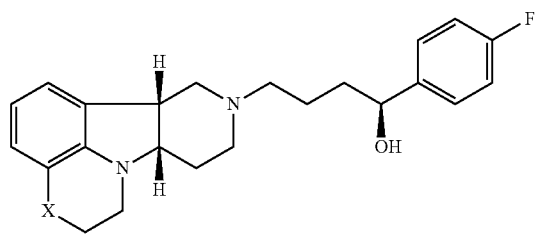

1.13. Composition I or any of 1.1, 1.3, 1.5 or 1.7, wherein the Compound of Formula I is:

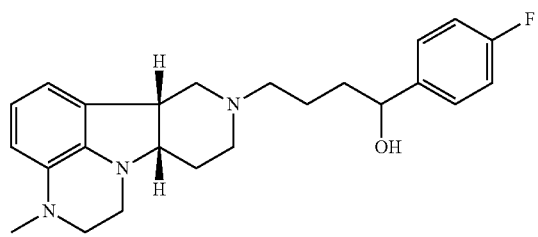 [SMILES: CN1CCN2c3c(cccc31)[C@@H]1CN(CCCC(O)c3ccc(F)cc3)CC[C@@H]12]

1.14. Composition I or any of 1.1, 1.3, 1.5 or 1.6, wherein the Compound of Formula I is:

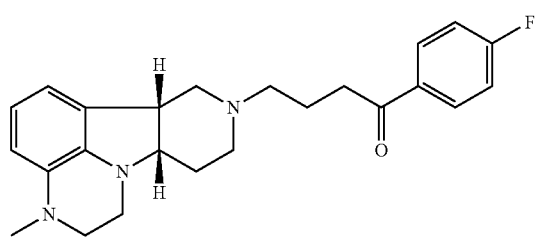 [SMILES: CN1CCN2c3c(cccc31)[C@@H]1CN(CCCC(=O)c3ccc(F)cc3)CC[C@@H]12]

1.15. Composition 1.14 wherein the Compound of Formula I is in the form of the tosylate salt.

1.16. Any foregoing Composition wherein, in the Compound of Formula II, $R_6$ is phenylamino or 4-fluorophenylamino.

1.17. Any foregoing Composition wherein, in the Compound of Formula II, $R_{10}$ is 3-fluoropyrid-2-yl or methylcarbonyl.

1.18. Any foregoing Composition wherein, in the Compound of Formula II, $R_6$ is phenylamino or 4-fluorophenylamino and $R_{10}$ is 3-fluoropyrid-2-yl or methylcarbonyl.

1.19. Any foregoing Composition wherein the Compound of Formula II is

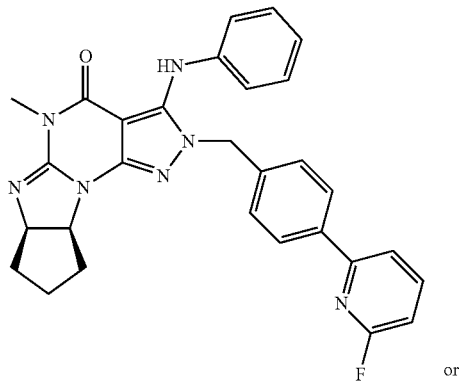

or

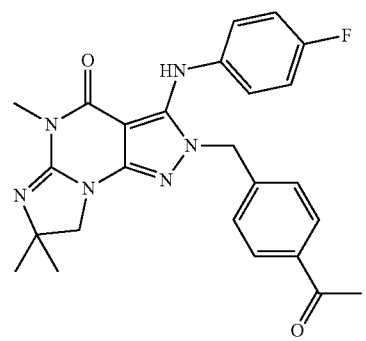

in free or pharmaceutically acceptable salt form.

1.20. Any foregoing Composition wherein the Compound of Formula II is in the form of the monophosphate salt.

1.21. Any foregoing Composition, wherein the Compound of Formula I is:

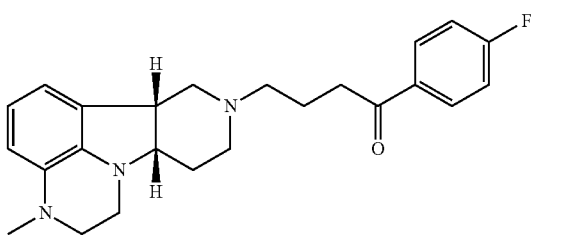 [SMILES: CN1CCN2c3c(cccc31)[C@@H]1CN(CCCC(=O)c3ccc(F)cc3)CC[C@@H]12]

in free of pharmaceutically acceptable salt form, e.g., tosylate salt form; and the Compound of Formula II is:

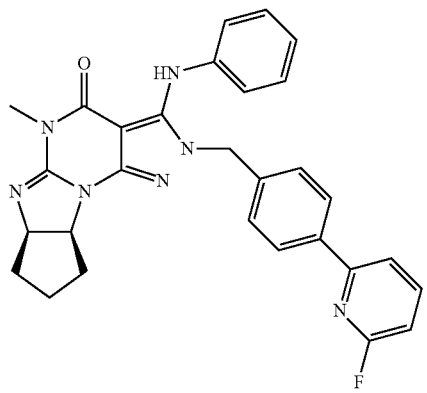 [SMILES: Cn1c(=O)/c(=C(/NCc2ccc(-c3cccc(F)n3)cc2)Nc2ccccc2)c(=N)n2c1=N[C@@H]1CCC[C@@H]12]

in free of pharmaceutically acceptable salt form, e.g., monophosphate salt form.

1.22. Any foregoing Composition comprising effective amounts of both a Compound of Formula I and a Compound of Formula II.

1.23. Any foregoing Composition in unit daily dosage form comprising 1 mg to 60 mg, e.g. 1 mg to 10 mg, e.g. 2 mg to 7 mg of the Compound of Formula 1.

1.24. Any foregoing Composition in unit daily dosage form comprising 0.1 mg to 10 mg e.g., 1mg to 5 mg, of the Compound of Formula II, 1.25. Any foregoing Composition further comprising a pharmaceutically acceptable diluent or carrier.

1.26. Any foregoing Composition in the form of a tablet.

1.27. Any foregoing Composition in the form of a capsule.

1.28. Any foregoing Composition in the form of a transdermal patch.

1.29. Any foregoing composition wherein the Compound of Formula I and the Compound of Formula II are in a bioerodable matrix, e.g., a bioerodable copolymer, for example poly(lactic-co-glycolic acid), e.g., for administration by injection to form a depot.

1.30. Any foregoing Composition in unit dosage form wherein the Compound of Formula I is:

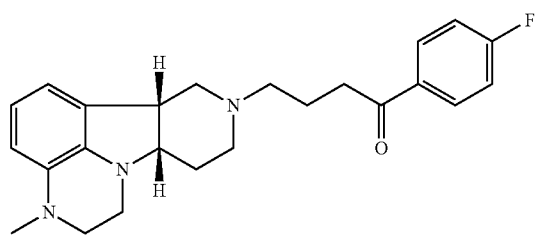 [SMILES: CN1CCN2c3c(cccc31)[C@@H]1CN(CCCC(=O)c3ccc(F)cc3)CC[C@@H]12]

in free or pharmaceutically acceptable salt form, in an amount of 1 mg to 10 mg, e.g., 2 mg to 7 mg, the dosage calculated as the free base equivalent;

and the Compound of Formula II is:

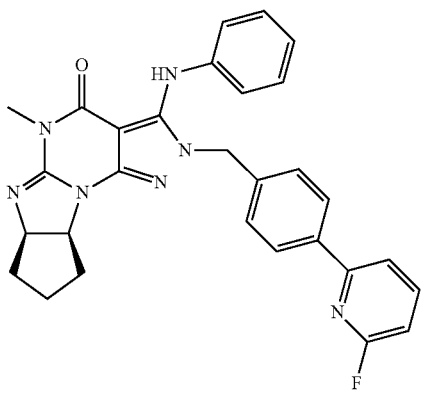 [SMILES: Cn1c(=O)/c(=C(/NCc2ccc(-c3cccc(F)n3)cc2)Nc2ccccc2)c(=N)n2c1=N[C@@H]1CCC[C@@H]12]

in free or pharmaceutically acceptable salt form, in an amount of 0.5 mg to 10 mg, e.g. 1 to 5 mg, the dosage calculated as the free base equivalent.

1.31. Composition 1.30 in the form of a tablet or capsule for oral administration comprising the compound of Formula I in tosylate salt form in an amount equivalent to 1 to 5 mg of free base, the compound of Formula II in monophosphate salt form in an amount equivalent to 0.5 to 2 mg of free base, and a pharmaceutically acceptable diluent or carrier.

1.32. Any foregoing Composition wherein the compound of Formula I and/or of Formula II is deuterated, e.g., wherein the deuterium:protium ratio at a specified position in the molecule is significantly higher, e.g., at least 2×, for example at least 10× higher, than above the natural isotope ratios.

1.33. Any foregoing Composition wherein the Compound of Formula I is a Compound of Formula 1 as described in WO 2015/154025, the contents of which are incorporated herein by reference, e.g., wherein the —CH$_2$-adjacent to X and or Y is —CHD- or —CD2-, wherein D signifies a deuterium hydrogen.

Any foregoing Composition for use in any of Methods 1, et seq. The disclosure further provides the use of a compound of Formula I as hereinbefore described in combination with a compound of Formula II as hereinbefore described, for use in the manufacture of a medicament, e.g., according to any of Composition 1, et seq., for use in any of Methods 1 et seq.

The 5-HT2A or 5-HT2A/D2 receptor ligand for use in the foregoing Methods and Compositions may for example be a 5-HT2A or 5-HT2A/D2 receptor ligand compound as disclosed in any of the following: U.S. Pat. Nos. 6,548,493; 7,238,690; 6,552,017; 6,713,471; U.S. RE39680, U.S. RE39679; for example as disclosed in U.S. Pat. No. 8,598,119, or WO 2011/133224 or WO 2015/154025, for example, a Compound of Formula I as described above. The compounds of Formula I and their pharmaceutically acceptable salts and salt crystals may be made using the methods as described and exemplified in any of the following patents or applications: U.S. Pat. Nos. 6,548,493; 7,238,690; 6,552,017; 6,713,471; U.S. RE39680; U.S. RE39679; PCT/US08/03340; U.S. application Ser. No. 10/786,935; WO 2009/114181 and WO 2011/133224, the contents of each of which are incorporated by reference in their entirety.

The Compounds of Formula I as hereinbefore described have a selective receptor profile wherein at low doses, e.g., 5-10 mg, they fully saturate the 5-HT2A receptors and only partially occupy (e.g. 5%-15% occupancy) the dopamine D2 receptors, and also bind to dopamine D2 receptors more extensively and to serotonin reuptake transporter (SERT) at a higher dose. Therefore the Compounds of the Invention are effective in treating one or more disorders associated with dementia, e.g., one or more disorders associated with mild cognition impairment and dementing illnesses including senile dementia, Alzheimer's disease, Pick's disease, frontotemporal dementia, parasupranculear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease, particularly behavioral/mood disturbances (e.g., agitation, aggressive/assaultive behavior) and sleep disorders, which are inadequately treated by the current marketed drugs for dementia and Alzheimer's disease, as well as treating psychosis and depressive disorders in patients suffering from dementia.

The PDE1 inhibitor may for example be a PDE1 inhibitor compound as disclosed in any of the following: WO 2006/133261, WO 2007/025103, WO 2007/143705, WO 2009/075784, WO 2009/073210, WO 2010/065153, WO 2010/065148, WO 2010/065151, WO 2010/065149, WO 2010/065147, WO 2010/065152, WO 2011/043816, WO 2011/153129, WO 2011/153135, WO 2011/153136, WO 2011/153138, WO 2012/171016, WO 2013/192556, WO 2014/151409, WO 2014/205354, or WO 2014/145617, for example as disclosed in WO 2009/075784, the contents of each of which are incorporated by reference herein in their entireties. For example, the PDE1 inhibitor may be a compound of Formula II as hereinbefore described.

The combinations as disclosed (i.e., of Compounds of Formula I and Formula II as hereinbefore described) may be administered simultaneously, separately or sequentially with one or more other active agents to treat dementia or dementing illnesses as hereinbefore described, particularly Alzheimer's disease or symptoms thereof.

The second or further therapeutic agents useful for the prophylaxis or treatment of dementia as hereinbefore described, particularly Alzheimer's disease, e.g., as described in Method 1 and 2 above, include but are not limited to a cholinesterase inhibitor and/or N-Methyl D-Asparate (NMDA) receptor antagonist.

Cholinesterase inhibitors, e.g., acetylcholinesterase inhibitors, are known in the art and/or are described e.g., in U.S. Pat. Nos. 4,895,841; and 4,948,807, the contents of each of which are incorporated by reference in their entirety. Preferred cholinesterase inhibitors to be used with the compound of the present invention include donepezil, rivastigmine, galantamine and tacrine.

NMDA receptor antagonists are also known in the art and are described in U.S. Pat. No. 5,061,703, the contents of which are incorporated by reference in their entirety. Preferred NMDA receptor antagonist to be used with the compound of the present invention is memantine.

Unlike dopamine receptor antagonists, Compounds of Formula I normalize brain dopamine activity, particularly in the prefrontal cortex. The Compounds of Formula I bind to 5-HT2A and dopamine D$_2$ receptors. Compounds of Formula I also exhibit nanomolar binding affinity for SERT compared to known antidepressants. Therefore, the compounds of Formula I are useful for the treatment of (1) behavioral or mood disorders such as agitation/irritation, aggressive/assaultive behavior, anger, physical or emotional outbursts; (2) psychosis; (3) depression; and (4) sleep disorders in patients suffering from dementia, particularly Alzheimer's disease. Therefore, in addition to the therapeutic agents useful for the treatment of dementia, the methods of the invention as hereinbefore described may optionally further comprises one or more therapeutic agents selected from antidepressant compounds, compounds that modulate GABA activity (e.g., enhances the activity and facilitates GABA transmission), a GABA-B agonist, a 5-HT modulator (e.g., a 5-HT$_{1A}$ agonist, a 5-HT2A antagonist, a 5-HT2A inverse agonist, etc.), a melatonin agonist, an ion channel modulator (e.g., blocker), a serotonin-2 antagonist/reuptake inhibitor (SARIs), an orexin receptor antagonist, an H3 antagonist, a noradrenergic antagonist, a galanin agonist, a CRH antagonist, human growth hormone, a growth hormone agonist, estrogen, an estrogen agonist, a neurokinin-1 drug, and an antipsychotic agent, e.g., an atypical antipsychotic agent, in free or pharmaceutically acceptable salt form. In such methods, the therapeutic agents may be adjunctive to the compounds of the invention. As used herein the term "adjunctive" refers to any treatment that is used in conjunction with another to increase the chance of cure, or to increase the first treatment's efficacy. In other words, adjunctive therapy acts as an aid to the primary treatment. The combinations of the invention can include mixtures of the combined drugs, as well as two or more separate compositions of the drugs, which individual compositions can be, for example, co-administered together to a patient at the same of different times.

The antidepressant useful for the invention may be selected from amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenelzine sulfate, protiptyline, sertraline, tranylcypromine, trazodone, trimipramine, and velafaxine, in free or pharmaceutically acceptable salt form. In certain embodiment, the antidepressant(s) is a selective serotonin reuptake inhibitor (SSRI). In a further embodiment, the SSRI compound is selected from the group consisting of citalopram, escitalopram oxalate, fluoxetine, fluvoxamine maleate, paroxetine, sertraline, and dapoxetine, in free or pharmaceutically acceptable salt form.

The dosages for combined therapy with a compound of Formula I, a compound of Formula II, and a further therapeutic agent can be the same as or lower than the approved dosage for the drug, the clinical or literature test dosage or the dosage used for the drug as a monotherapy. In a specific embodiment, the dosages of a compound of Formula I of Formula II, and/or the additional therapeutic agents are lower than when used in a monotherapy.

The term "GABA" refers to gamma-aminobutyric acid. The GABA compounds are compounds which bind to the GABA receptor, and include, but are not limited to one or more of doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gabaxadol, vigabatrin, tiagabine, EVT 201 (Evotec Pharmaceuticals) or estazolam.

5HT$_{2A}$ antagonists include ketanserin, risperidone, eplivanserin, volinanserin (Sanofi-Aventis, France), pruvanserin, pimavanserin (ACP-103), MDL 100907 (Sanofi-Aventis, France), HY10275 (Eli Lilly), APD125 (Arena Pharmaceuticals, San Diego, Calif.), AVE8488 (Sanofi-Aventis, France) and pizotifen.

5HT$_{1A}$ agonists include repinotan, sarizotan, eptapirone, buspirone and MN-305 (MediciNova, San Diego, Calif.).

Melatonin agonists include melatonin, ramelteon (ROZEREM®, Takeda Pharmaceuticals, Japan), VEC-162 (Vanda Pharmaceuticals, Rockville, Md.), PD-6735 (Phase II Discovery) and agomelatine.

Ion channel blockers such as lamotrigine, gabapentin or pregabalin.

Orexin receptor antagonists include orexin, a 1,3-biarylurea, SB-334867-a (GlaxoSmithKline, UK), GW649868 (GlaxoSmithKline) and a benzamide derivative, for example.

Serotonin-2 antagonist/reuptake inhibitors (SARI) include Org 50081 (Organon—Netherlands), ritanserin, nefazodone, serzone and trazodone.

Neurokinin-1 drugs include Casopitant (GlaxoSmithKline).

Specific examples of additional therapeutic agents useful for the current invention include modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, zolpidem, gabaxadol, vigabatrin, tiagabine, EVT 201 (Evotec Pharmaceuticals), estazolam, ketanserin, risperidone, eplivanserin, volinanserin (Sanofi-Aventis, France), pruvanserin, pimavanserin (ACP-103), pizotifen, MDL 100907 (Sanofi-Aventis, France), HY10275 (Eli Lilly), APD125 (Arena Pharmaceuticals, San Diego, Calif.), AVE8488 (Sanofi-Aventis, France), repinotan, sarizotan, eptapirone, buspirone, MN-305 (MediciNova, San Diego, Calif.), melatonin, ramelteon (ROZEREM®, Takeda Pharmaceuticals, Japan), VEC-162 (Vanda Pharmaceuticals, Rockville, Md.), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon—Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, velafaxine, chlorpromazine, haloperidol, droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone, ziprasidone and paliperidone, asenapine, lurasidone, iloperidone and cariprazine, in free or pharmaceutically acceptable salt form.

If not commercially available, starting materials for these processes may be made using techniques similar or analogous to the synthesis of known compounds. All references cited herein are hereby incorporated in their entirety by reference.

The words "treatment" and "treating" are to be understood accordingly as embracing prophylaxis and treatment or amelioration of symptoms of disease and/or treatment of the cause of the disease. In particular embodiment, the word "treatment" and "treating" refers to prophylaxis or amelioration of symptoms of the disease.

The term "patient" may include a human or non-human patient.

The term "dementia" is intended to refer to a condition or disorder characterized by the loss of cognitive ability affecting memory, thinking, language, judgment and behavior. Early symptoms of dementia may include difficulty performing tasks that require some thought (balancing a checkbook, playing games (such as bridge); learning new information; getting lost on familiar routes; having language difficulties (difficulties in finding name of familiar objects); losing interest in things previously enjoy; losing social skills. More severe symptoms of dementia include change in sleep patterns, often waking up at night; difficulty performing basic tasks such as brushing teeth or preparing a meal; forgetting details about current events; having hallucinations, violent behavior, delusions, depression, agitation; difficulty reading or writing; having poor judgment or loss of ability to recognize danger; losing the ability to recognize family members or understand language. The term "dementia" refers to any of the dementing illnesses as described herein regardless of etiology and therefore shall include but not limited to mild or severe cognition impairment and dementing illnesses such as senile dementia, Alzheimer's disease, Pick's disease, frontotemporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease. In a particular embodiment, dementia refers to mild cognitive impairment. In another embodiment, dementia refers to Alzheimer's disease.

The term "disorder associated with dementia" means common co-morbid psychiatric disorders or conditions associated with dementia, which include but not limited to (1) behavioral or mood disorders such as agitation/irritation, aggressive/assaultive behavior, anger, physical or emotional outbursts; (2) psychosis; (3) depression; and (4) sleep disorders. In particular embodiment of the invention, the disorders associated with dementia are disorders associated Alzheimer's disease.

The term "mild cognitive impairment" or "mild cognition impairment" (MCI, also known as incipient dementia, or isolated memory impairment) is cognitive impairment beyond that expected based on the age and education of the individual, but which is not significant enough to interfere with their daily activities. Symptoms of MCI include difficulty performing more than one task at a time, solving problems or making decisions, forgetting recent events or conversations and taking longer to perform more difficult mental activities.

If not otherwise specified or clear from context, the following terms herein have the following meanings:

"Alkyl" as used herein is a saturated or unsaturated hydrocarbon moiety, e.g., one to twenty-one carbon atoms in length, which may be linear or branched (e.g., n-butyl or tert-butyl), preferably linear, unless otherwise specified. For example, "$C_{1-21}$ alkyl" denotes alkyl having 1 to 21 carbon atoms. In one embodiment, alkyl is optionally substituted with one or more hydroxy or $C_{1-22}$alkoxy (e.g., ethoxy) groups. In another embodiment, alkyl contains 1 to 21 carbon atoms, preferably straight chain and optionally saturated or unsaturated, for example $R_1$ is an alkyl chain containing 1 to 21 carbon atoms, preferably 6-15 carbon atoms, 16-21 carbon atoms, e.g., so that together with the —C(O)— to which it attaches, e.g., when cleaved from the compound of Formula I, forms the residue of a natural or unnatural, saturated or unsaturated fatty acid.

The 5-HT2A or 5-HT2A/D2 receptor ligand, for example a substituted heterocycle fused gamma-carbolines as described herein and/or the PDE1 inhibitor for use in the Methods and Compositions of the disclosure may be in free, pharmaceutically acceptable salt or prodrug form. Pharmaceutically acceptable salts include, for example, the tosylate salts in the case of Compounds of Formula 1, the phosphate salts in the case of Compounds of Formula II, and other salts as described above. Where dosages or amounts of a salt are given by weight, e.g., milligrams per day or milligrams per unit dose, the dosage amount of the salt is given as the weight of the corresponding free base, unless otherwise indicated.

The 5-HT2A or 5-HT2A/D2 receptor ligand and/or the PDE1 inhibitor may in some cases also exist in prodrug form. A prodrug form is compound which converts in the body to the active compound. For example compounds which contain hydroxy or carboxy substituents may form physiologically hydrolysable and acceptable esters. As used herein, "physiologically hydrolysable and acceptable ester" means esters which are hydrolysable under physiological conditions to yield acids (in the case of compounds which have hydroxy substituents) or alcohols (in the case of compounds which have carboxy substituents) which are themselves physiologically tolerable at doses to be administered. For example, wherein Y of the compound of Formula I is —C(H)(OR$_1$), and R$_1$ is —C(O)—C$_{1-21}$alkyl, e.g., —C(O)—C$_3$alkyl or —C(O)—C$_9$alkyl, these compounds may hydrolyze under physiological condition to yield a compound of Formula I wherein Y is —C(H)(OH) on the one hand and C$_{1-21}$alkyl-C(O)OH, e.g., C$_3$alkyl-C(O)OH or C$_9$alkyl-C(O)OH on the other hand. As will be appreciated the term thus embraces conventional pharmaceutical prodrug forms. Wherein a prodrug (e.g., the compound of formula (I) wherein R$_1$ is —C(O)—C$_{1-21}$alkyl) is used, the dosage amount is calculated based on the amount of the compound of formula (I) wherein Y is —C(=O)— or —CH(OH)—, in free base form.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

The phrase "disorder(s) associated with Alzheimer's disease" includes, but is not limited to (1) behavioral or mood disorders such as agitation/irritation, aggressive/assaultive behavior, anger, physical or emotional outbursts; (2) psychosis; (3) depression; and (4) sleep disorders in patients suffering from Alzheimer's disease.

Dosages employed in practicing the present invention will of course vary depending, e.g. on the particular disease or condition to be treated, the particular active compounds used, the mode of administration, and the therapy desired. Unless otherwise indicated, an amount of an active compound for administration (whether administered as a free base or as a salt form) refers to or is based on the amount of the compound in free form (i.e., the calculation of the amount is based on the amount of active moiety in free form, not taking into account the weight of the counter ion in the case of a salt). Wherein a prodrug (e.g., the compound of formula (I) wherein R$_1$ is —C(O)—C$_{1-21}$alkyl) is used, the dosage amount is calculated based on the amount of the compound of formula (I) wherein Y is C(=O) in free base form. Compounds of the Invention may be administered by any suitable route, including orally, intra-muscularly, subcutaneously, parenterally or transdermally, but are preferably administered orally. Compounds of the Invention may be administered by any suitable route, including orally, parenterally or transdermally, but are preferably administered orally.

For the avoidance of doubt, any disclosure of a numerical range, e.g., "up to X" amount is intended to include the upper numerical limit X. Therefore, a disclosure of "up to 60 mg" is intended to include 60 mg.

Pharmaceutical compositions comprising compounds of the Invention may be prepared using conventional diluents or excipients and techniques known in the galenic art. Thus oral dosage forms may include tablets, capsules, solutions, suspensions and the like.

The invention claimed is:

1. A method for the treatment of one or more disorders associated with dementia comprising administering to a patient in need thereof, a therapeutically effective amount of (i) a 5-HT2A or 5-HT2A/D2 receptor ligand and (ii) a PDE1 inhibitor;

wherein the 5-HT2A or 5-HT2A/D2 receptor ligand is a compound of Formula I:

Formula I

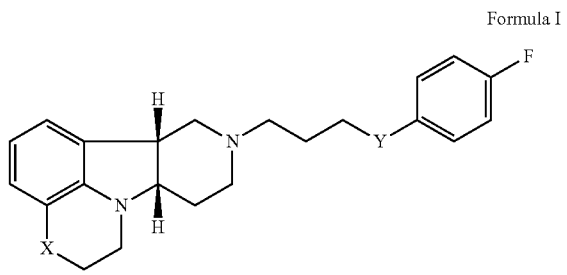

wherein:
X is —N(H)—, —N(CH$_3$)— or —O—;
Y is —C(=O), —C(H)(OH) or —C(H)(OR$_1$);
R$_1$ is —C(O)—C$_{1-21}$alkyl, optionally saturated or unsaturated and optionally substituted with one or more hydroxy or C$_{1-22}$alkoxy, wherein such compound hydrolyzes to form the residue of a natural or unnatural, saturated or unsaturated fatty acid,
in free, pharmaceutically acceptable salt or prodrug form; and
wherein the PDE1 inhibitor is a compound according to Formula II Formula II

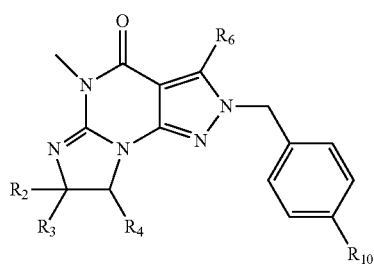

wherein
R$_2$ is H and R$_3$ and R$_4$ together form a tri- or tetra-methylene bridge; or R$_2$ and R$_3$ are each methyl and R$_4$ is H; or R$_2$ and R$_4$ are H and R$_3$ is isopropyl;
R$_6$ is optionally halo-substituted phenylamino or optionally halo-substituted benzylamino;
R$_{10}$ is optionally halo-substituted phenyl, optionally halo-substituted pyridyl, or thiadiazolyl;
in free or pharmaceutically acceptable salt form.

2. The method of claim 1, wherein the Compound of Formula I is

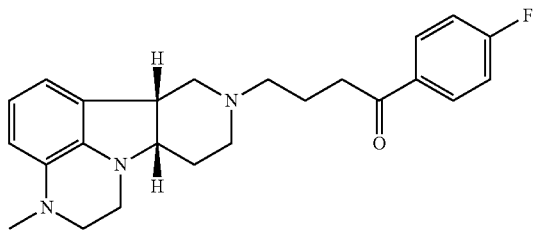 [SMILES: CN1CCN2c3c(cccc31)[C@@H]1CN(CCCC(=O)c3ccc(F)cc3)CC[C@@H]12]

in free or pharmaceutically acceptable salt form.

3. The method of claim 1, wherein the Compound of Formula II is

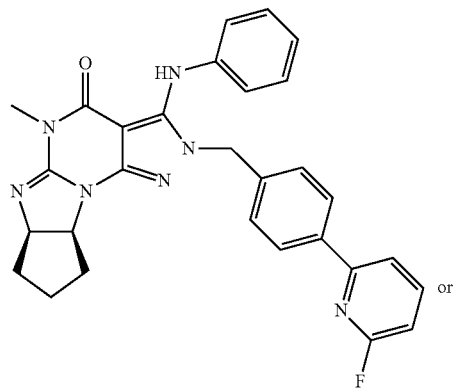

or

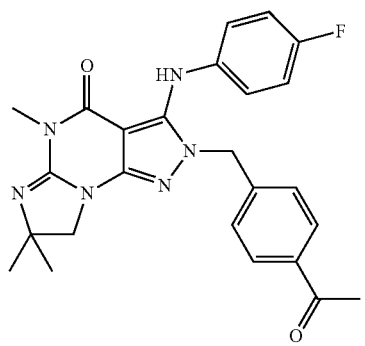

in free or pharmaceutically acceptable salt form.

4. The method of claim 1, wherein the method comprises administration of a pharmaceutical composition comprising effective amounts of both the Compound of Formula I and the Compound of Formula II.

5. The method of claim 1, wherein the daily dosage of the Compound of Formula I is 1 mg to 10 mg.

6. The method of claim 1, wherein the daily dosage of the Compound of Formula II is 0.1 mg to 10 mg.

7. The method of claim 1, wherein the Compound of Formula I is:

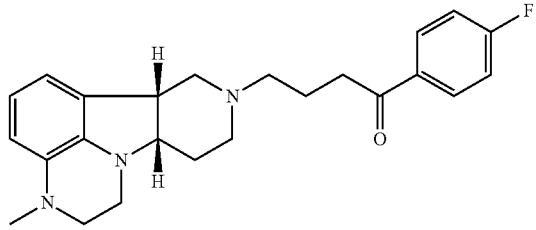 [SMILES: CN1CCN2c3c(cccc31)[C@@H]1CN(CCCC(=O)c3ccc(F)cc3)CC[C@@H]12]

in free or pharmaceutically acceptable salt form, administered in a daily dose of 1 mg to 10 mg, the dosage calculated as the free base equivalent;
and the Compound of Formula II is:

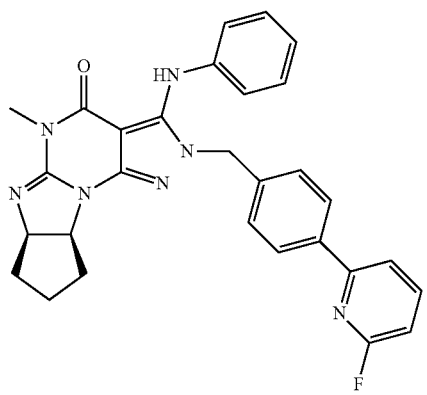 [SMILES: Cn1c(=O)/c(=C(/NCc2ccc(-c3cccc(F)n3)cc2)Nc2ccccc2)c(=N)n2c1=N[C@@H]1CCC[C@@H]12]

in free or pharmaceutically acceptable salt form, administered in a daily dose of 0.5 mg to 10 mg, the dosage calculated as the free base equivalent.

8. The method of claim 7, wherein the compound of Formula I is in tosylate salt form administered in a daily dose equivalent to 1 to 5 mg of free base and the compound of Formula II is in monophosphate salt form administered in a daily dose equivalent to 0.5 to 2 mg of free base.

9. The method of claim 8, wherein the method comprises once daily administration of a unit dosage for oral administration, comprising the compound of Formula I in tosylate salt form in an amount equivalent to 1 to 5 mg of free base, the compound of Formula II in monophosphate salt form in an amount equivalent to 0.5 to 2 mg of free base, and a pharmaceutically acceptable diluent or carrier.

10. The method of claim 1, wherein the one or more disorders associated with dementia are selected from disorders associated with mild to severe cognition impairment and dementing illnesses including senile dementia, Alzheimer's disease, Pick's disease, frontotemporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease.

11. The method of claim 1, wherein the disorders associated with dementia include one or more of behavioral or mood disturbances, psychosis, depression and/or sleep disturbances.

12. The method of claim 1, comprising enhancing cognition in a patient with dementia.

13. The method of claim 1, wherein the disorder is Alzheimer's disease or symptoms thereof.

14. A pharmaceutical composition comprising a therapeutically effective amount of (i) a 5-HT2A or 5-HT2A/D2 receptor ligand and (ii) a PDE1 inhibitor wherein the 5-HT2A or 5-HT2A/D2 receptor ligand is a compound of Formula I:

Formula I

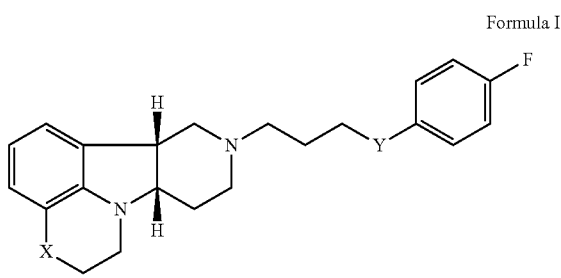

wherein:

X is —N(H)—, —N(CH$_3$)— or —O—;

Y is —C(=O), —C(H)(OH) or —C(H)(OR$_1$);

R$_1$ is —C(O)—C$_{1-21}$alkyl, optionally saturated or unsaturated and optionally substituted with one or more hydroxy or C$_{1-22}$alkoxy groups, wherein such compound hydrolyzes to form the residue of a natural or unnatural, saturated or unsaturated fatty acid, in free, pharmaceutically acceptable salt or prodrug form; and wherein the PDE1 inhibitor is a compound according to Formula II Formula II

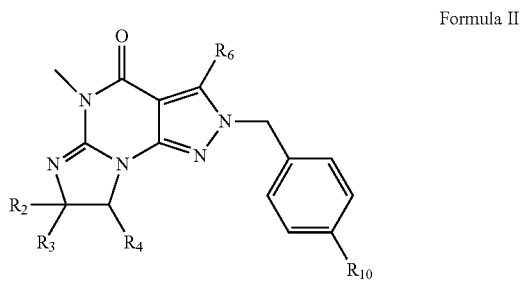

wherein

R$_2$ is H and R$_3$ and R$_4$ together form a tri- or tetramethylene bridge; or R$_2$ and R$_3$ are each methyl and R$_4$ is H; or R$_2$ and R$_4$ are H and R$_3$ is isopropyl;

R$_6$ is optionally halo-substituted phenylamino or optionally halo-substituted benzylamino;

R$_{10}$ is optionally halo-substituted phenyl, optionally halo-substituted pyridyl, or thiadiazolyl;

in free or pharmaceutically acceptable salt form.

15. The pharmaceutical composition of claim 14, wherein the Compound of Formula I is

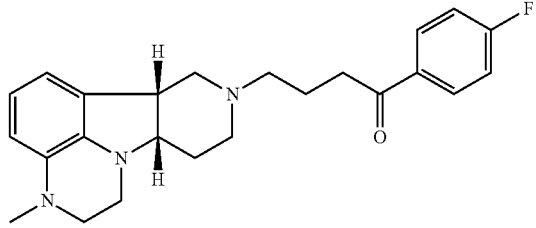 [SMILES: CN1CCN2c3c(cccc31)[C@@H]1CN(CCCC(=O)c3ccc(F)cc3)CC[C@@H]12]

in free or pharmaceutically acceptable salt form.

16. The pharmaceutical composition of claim 14, wherein the Compound of Formula II is

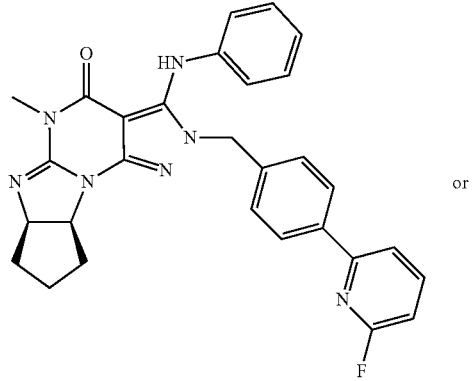

or

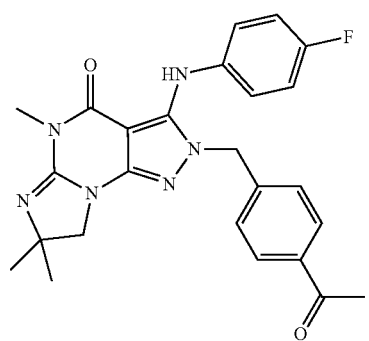

in free or pharmaceutically acceptable salt form.

17. The pharmaceutical composition of claim 14, further comprising a pharmaceutically acceptable diluent or carrier.

18. The pharmaceutical composition of claim 14, in the form of a tablet, capsule, or transdermal patch.

19. The pharmaceutical composition of claim 14, comprising the Compound of Formula I and the Compound of Formula II in a bioerodable matrix.

20. The pharmaceutical composition of claim 14, in unit dosage form wherein the Compound of Formula I is:

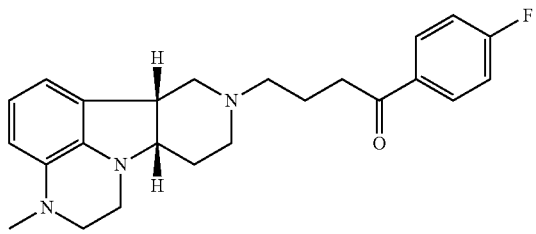 [SMILES: CN1CCN2c3c(cccc31)[C@@H]1CN(CCCC(=O)c3ccc(F)cc3)CC[C@@H]12]

in free or pharmaceutically acceptable salt form, in an amount of 1 mg to 10 mg, the dosage calculated as the free base equivalent; and
the Compound of Formula II is:

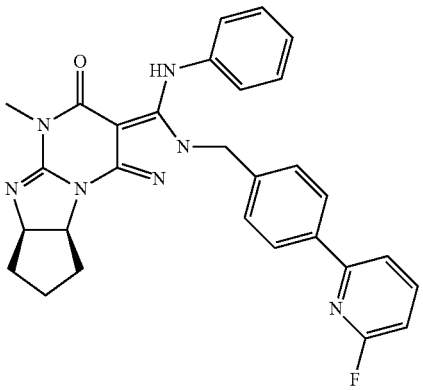 [SMILES: Cn1c(=O)/c(=C(/NCc2ccc(-c3cccc(F)n3)cc2)Nc2ccccc2)c(=N)n2c1=N[C@@H]1CCC[C@@H]12]

in free or pharmaceutically acceptable salt form, in an amount of 0.5 mg to 10 mg, the dosage calculated as the free base equivalent.

21. The pharmaceutical composition of claim 20 in the form of a tablet or capsule for oral administration comprising the compound of Formula I in tosylate salt form in an amount equivalent to 1 to 5 mg of free base, the compound of Formula II in monophosphate salt form in an amount equivalent to 0.5 to 2 mg of free base, and a pharmaceutically acceptable diluent or carrier.

22. The method of claim 1, wherein the compound of Formula I and the compound of Formula II are comprised together in a pharmaceutical composition further comprising a pharmaceutically acceptable diluent or carrier.

23. The method of claim 2, wherein the compound of Formula I and the compound of Formula II are comprised together in a pharmaceutical composition further comprising a pharmaceutically acceptable diluent or carrier.

24. The method of claim 3, wherein the compound of Formula I and the compound of Formula II are comprised together in a pharmaceutical composition further comprising a pharmaceutically acceptable diluent or carrier.

25. The method of claim 7, wherein the compound of Formula I and the compound of Formula II are comprised together in a pharmaceutical composition further comprising a pharmaceutically acceptable diluent or carrier.

26. The method of claim 8, wherein the compound of Formula I and the compound of Formula II are comprised together in a pharmaceutical composition further comprising a pharmaceutically acceptable diluent or carrier.

* * * * *